(12) United States Patent
Kabanov et al.

(10) Patent No.: US 6,277,410 B1
(45) Date of Patent: Aug. 21, 2001

(54) COPOLYMER COMPOSITIONS FOR ORAL DELIVERY

(75) Inventors: Alexander V. Kabanov, Omaha, NE (US); Valery Y. Alakhov, Quebec (CA); Elena V. Batrakova, Omaha, NE (US)

(73) Assignee: Supratek Pharma Inc. (CA)

(*) Notice: Subject to any disclaimer, the term of this patent is extended or adjusted under 35 U.S.C. 154(b) by 0 days.

(21) Appl. No.: 09/019,648

(22) Filed: Feb. 6, 1998

Related U.S. Application Data

(63) Continuation-in-part of application No. 08/478,879, filed on Jun. 7, 1995, now Pat. No. 6,153,193, and a continuation-in-part of application No. 08/951,079, filed on Oct. 15, 1997, now Pat. No. 5,840,319, which is a division of application No. 08/478,978, filed on Jun. 7, 1995, now Pat. No. 5,817,321, which is a continuation-in-part of application No. 08/374,406, filed on Jan. 17, 1995, now abandoned, which is a continuation of application No. 07/957,998, filed on Oct. 8, 1992, now abandoned.

(51) Int. Cl.⁷ .................................................. A61K 38/17

(52) U.S. Cl. .................. 424/486; 424/422; 514/772.1; 514/772.3

(58) Field of Search ................................ 424/486, 422; 514/772.3, 772.1

(56) References Cited

U.S. PATENT DOCUMENTS

| | | | |
|---|---|---|---|
| 4,027,013 | 5/1977 | Bick et al. | 424/101 |
| 4,106,474 | 8/1978 | Hunter et al. | 126/110 R |
| 4,188,373 | 2/1980 | Krezanoski | 424/78 |
| 4,474,752 | 10/1984 | Haslam et al. | 434/78 |
| 4,485,457 | 11/1984 | Balaska et al. | 463/45 |
| 4,609,546 | 9/1986 | Hiratani | 424/83 |
| 4,740,498 | 4/1988 | Hirao et al. | 514/8 |
| 4,772,466 | 9/1988 | Alison et al. | 424/88 |
| 4,801,452 | 1/1989 | Hunter et al. | 424/94.63 |
| 4,837,014 | 6/1989 | Hunter et al. | 424/94.63 |

(List continued on next page.)

FOREIGN PATENT DOCUMENTS

| | | |
|---|---|---|
| 0211601 | 2/1997 | (EP) . |
| 86/07539 | * 12/1986 | (WO) . |
| 88/01873 | * 3/1988 | (WO) . |
| 88/06038 | * 8/1988 | (WO) . |
| WO89/00812 | 2/1989 | (WO) . |
| 91/16058 | * 10/1991 | (WO) . |
| 92/00101 | * 1/1992 | (WO) . |
| 92/16484 | * 10/1992 | (WO) . |
| WO94/08564 | 4/1994 | (WO) . |
| WO95/03829 | 2/1995 | (WO) . |
| WO6/00801 | 7/1996 | (WO) . |
| WO96/40056 | 12/1996 | (WO) . |
| WO99/39731 | 8/1999 | (WO) . |

OTHER PUBLICATIONS

Hunter et al. The Adjuvant Activity of Nonionic Block Polymer Surfactants (Journal of Immunology, 133(6), pp. 3167–3175), 1984.*

Kabanov et al., "Polymeric Surfactant Micelles As Microcontainers . . . ," *Journal of Neuroimmuno.* (Suppl 1): 130 (1991).

Chawla et al., "Aggregation of Insulin, Containing Surfactants, in Contact with Different Materials," Diabetes. vol. 34: 420–424 (1995).

(List continued on next page.)

*Primary Examiner*—Richard L. Raymond
(74) *Attorney, Agent, or Firm*—Mathews, Collins, Shepherd & Gould, P.A.

(57) ABSTRACT

Compositions for oral delivery having a biological agent or protein, peptide, or derivative thereof, and a poly(oxyethylene)-poly(oxypropylene) block copolymer. The compositions are useful in oral delivery of numerous agents. The invention also encompasses methods of treatment using the same.

18 Claims, 4 Drawing Sheets

U.S. PATENT DOCUMENTS

| | | | |
|---|---|---|---|
| 4,865,835 | | 9/1989 | Begent .................................... 424/1.1 |
| 4,873,083 | | 10/1989 | Hunter et al. ........................ 424/1.49 |
| 4,879,109 | | 11/1989 | Hunter ................................. 514/723 |
| 4,882,168 | | 11/1989 | Casey et al. ........................... 514/21 |
| 4,897,263 | | 1/1990 | Hunter ................................. 514/723 |
| 4,937,070 | | 6/1990 | Hunter .............................. 424/78.38 |
| 4,957,735 | | 9/1990 | Huang ................................ 424/85.8 |
| 4,997,644 | | 3/1991 | Hunter .............................. 424/78.35 |
| 5,017,370 | | 5/1991 | Hunter et al. ..................... 424/78.38 |
| 5,028,599 | | 7/1991 | Hunter .............................. 424/78.38 |
| 5,030,448 | | 7/1991 | Hunter .............................. 424/78.38 |
| 5,032,394 | | 7/1991 | Hunter .............................. 424/78.38 |
| 5,039,520 | | 8/1991 | Hunter .............................. 424/78.38 |
| 5,041,288 | | 8/1991 | Hunter .............................. 424/78.38 |
| 5,047,236 | | 9/1991 | Hunter et al. ..................... 424/78.38 |
| 5,064,643 | | 11/1991 | Hunter et al. ..................... 424/78.38 |
| 5,071,649 | | 12/1991 | Hunter .............................. 424/78.38 |
| 5,078,995 | | 1/1992 | Hunter et al. ..................... 424/78.38 |
| 5,080,894 | | 1/1992 | Hunter et al. ..................... 424/78.38 |
| 5,089,260 | | 2/1992 | Hunter et al. ..................... 424/78.38 |
| 5,114,708 | | 5/1992 | Hunter et al. ........................ 514/716 |
| 5,152,979 | | 10/1992 | Hunter .............................. 424/78.38 |
| 5,182,106 | | 1/1993 | Mezrow et al. ................... 424/78.34 |
| 5,183,687 | | 2/1993 | Hunter et al. ..................... 424/78.34 |
| 5,198,211 | | 3/1993 | Hunter et al. ..................... 424/78.31 |
| 5,234,683 | | 8/1993 | Hunter et al. ..................... 424/78.31 |
| 5,240,701 | | 8/1993 | Hunter et al. ..................... 424/78.31 |
| 5,240,702 | | 8/1993 | Hunter et al. ..................... 424/78.31 |
| 5,250,294 | | 10/1993 | Hunter et al. ..................... 424/78.31 |
| 5,399,363 | * | 3/1995 | Liversedge et al. ................. 424/490 |
| 5,417,982 | | 5/1995 | Modi .................................... 424/486 |
| 5,436,170 | | 7/1995 | Cornell et al. ....................... 436/527 |
| 5,449,513 | | 9/1995 | Yokoyama et al. .............. 424/78.08 |
| 5,466,445 | | 11/1995 | Hunter .............................. 424/78.31 |
| 5,470,568 | | 11/1995 | Lee .................................... 424/78.02 |
| 5,488,034 | | 1/1996 | McGregor et al. ................... 514/12 |
| 5,494,660 | | 2/1996 | Hunter et al. ..................... 424/78.31 |
| 5,523,492 | * | 6/1996 | Emanuele et al. ................... 568/624 |
| 5,531,925 | | 7/1996 | Landh et al. ..................... 252/299.01 |
| 5,554,372 | * | 9/1996 | Hunter .............................. 424/280.1 |
| 5,567,859 | * | 10/1996 | Emanuele et al. ................... 568/624 |
| 5,573,934 | | 11/1996 | Hubbel et al. ....................... 435/177 |
| 5,591,715 | * | 1/1997 | Coon et al. ........................... 514/10 |
| 5,622,649 | * | 4/1997 | Hunter et al. ......................... 516/29 |
| 5,648,071 | * | 7/1997 | Hunter et al. ..................... 424/78.31 |
| 5,656,611 | | 8/1997 | Kabanov et al. ....................... 514/44 |
| 5,674,911 | * | 10/1997 | Emmanuele et al. ................. 514/723 |
| 5,691,387 | * | 11/1997 | Emanuele et al. ................... 514/723 |
| 5,696,090 | | 12/1997 | McGregor et al. ..................... 514/12 |
| 5,696,298 | * | 12/1997 | Emanuele et al. ................... 568/623 |
| 5,698,529 | | 12/1997 | Alakhov et al. ....................... 514/12 |
| 5,776,891 | * | 7/1998 | Coon et al. ............................ 514/10 |
| 5,840,319 | | 11/1998 | Alakhov et al. ..................... 424/400 |
| 5,885,590 | | 3/1999 | Hunter et al. ..................... 424/280.1 |
| 6,040,295 | | 3/2000 | Rolland et al. ........................ 514/44 |

OTHER PUBLICATIONS

Kabanov et al., "Interpolyelectrolyte and Block Ionomer Complexes for Gene Delivery: Physicochemical Aspects," Advanced Drug Delivery Reviews, Elsevier, vol. 30: 49–60 (1998).

Batralova, "Effects of Pluronic Block Copolymers on Drug Absorption in Caco–2 Cell Monolayers," Pharmaceutical Research, vol. 15, No. 6, (1998).

Abstract, Database WPI Week 9519, Derwent Publ. Ltd. AN 95–144714 High Water Soluble Antitumour Adriamycin Agent Comprise Micellar Complex Block Copolymer Polyethyene Glycol Poly Amino acid (1995).

Kataoka et al., "Block Copolymer Micelles As Vehicles for Drug Delivery,"*Journal of Controlled Release*, vol. 24: 119–132 (1993).

Chekhonin et al., "Fatty Acid Acylated Fab–Fragments of Antibodies To Neurospecific Proteins As Carriers For Neuroleptic Targeted Delivery In Brain", *FEBS Lett.*, 287, N 1,2, 149–152 (1991).

Kabanov et al., "The Neuroleptic Activity Of Haloperidol Increases After Its Solubilization In Surfactant Micelles: Micelles As Microcontainers For Drug Targeting", *FEBS Lett.*, 258, N 2, 343–345 (1989).

Kabanov et al., "A New Class Of Drug Carriers: Micelles Of Poly(oxyethylene)—Poly(oxypropylene) Block Copolymers As Microcontainers For Drug Targeting From Blood In Brain", *J. Contr. Release*, 22, 141–158 (1992).

Kabanov et al., "Enhancement Of Macromolecule Penetration Into Cells And Nontraditional Drug Delivery Systems", *Sov. Sci. Rev. D. Physicochem. Biol.* (V.P. Skulachev ed.), vol. 11, Glasgow: Harwood Academic Publishers, part 2, pp. 1–77 (1992).

Kabanov et al., "Site Specific Drug Targeting", *CPhI '92 Conference Proceedings*, London: Eyre & Spotiswoode Ltd., pp. 89–96 (1993).

* cited by examiner

COPOLYMER COMPOSITIONS FOR ORAL DELIVERY

This application is a continuation-in-part of U.S. application Ser. No. 08/478,979, filed Jun. 7, 1995, now U.S. Pat. No. 6,153,193, and U.S. application Ser. No. 08/951,079, filed Oct. 15, 1997, now U.S. Pat. No. 5,840,319, which is a divisional of U.S. application Ser. No. 08/478,978 filed Jun. 7, 1995, now U.S. Pat. No. 5,817,321, which is a continuation-in-part of 08/374,406, filed Jan. 17, 1995, now abandoned, which in turn is a continuation of U.S. application Ser. No. 07/957,998, filed Oct. 8, 1992, now abandoned.

FIELD OF THE INVENTION

The invention relates to copolymer pharmaceutical compositions useful in oral administration of a number of biological agents.

BACKGROUND OF THE INVENTION

A variety of biological agents are currently in use for the treatment of diseases and disorders. Many of these agents may be administered topically, rectally, vaginally, by pulmonary route, or parenterally.

However, parenteral administration (such as intramuscular, subcutaneous, intraperitoneal, intra-arterial or intravenous) as well as rectal, vaginal, and pulmonary routes, are often inconvenient, costly, or both. Oral administration thus possesses several advantages over these other routes. It is a convenient, cost-effective mode of administration for the patient.

The present invention relates, among other things, to (1) pharmaceutical compositions and methods for chemotherapeutic agents and (2) pharmaceutical compositions for biological agents, particularly those whose target cells or tissues are resistant to the biological agent.

A number of chemotherapeutic agents exhibit low solubility and stability in physiological fluids. Often, chemotherapeutic agents are poorly transported across cell membranes. Further, many of these agents are binding with plasma proteins as well as other nonspecific interactions in the blood stream before they can reach the target cancer.

Multi-Drug Resistance

A major roadblock to effective chemotherapeutic treatments is the resistance to biological agents that many neoplasms and microbial infections develop. The sensitivity of neoplastic cells to anti-cancer agents can decrease by a factor as high as $10^3$ during the course of a chemotherapeutic regimen. When such resistance develops with respect to one agent, often the target cells are found to also be resistant to a number of other biological agents to which they had not previously been exposed. See Goldstein et al., *Crit. Rev. Oncol. Hematol.*, 12:243–253 (1992); *Goodman and Gilman's The Pharmacological Basis of Therapeutics*, 8th Ed., McGraw-Hill, New York, 1994. One mechanism by which such resistance develops is believed to involve the membrane pump protein gp-170 (a glycoprotein P or P-gp protein). See Goldstein et al., *Crit. Rev. Oncol. Hematol.*, 12:243–253 (1992).

It has now been discovered that these difficulties can be overcome by administering the biological agent in question in a formulation containing micelles of one or more block copolymers with the characteristics described below. Further, it has now been discovered that a certain subset of these block copolymers is particularly effective in delivering drugs and reversing resistance to a biological agent.

The Blood Brain Barrier

The brain is isolated from circulatory blood because the endothelial cell lining of blood vessels in the brain is more selective than it is in other parts of the body with respect to the molecules that are allowed to diffuse into the interstitial space of the brain. The mechanism that isolates the brain is often referred to as a "blood-brain barrier." As a result of the blood-brain barrier, biological agents that are intended to affect the brain or a disease in the brain often must be administered in high dosage to compensate for the diffusion barrier provided by the blood-brain barrier. Animals to whom the high doses are administered are at greater risk of experiencing toxic or other side effects. It is therefore desirable to enhance the permeability of chemotherapeutic agents across the blood-brain barrier. See, *Goodman's and Gilman's The Pharmacological Basis of Therapeittics*, Eighth Edition, p.11.

In the brain and in other tissues it is often desirable to target a biological agent to a particular tissue at which the agent is anticipated to beneficially act. This desirability is particularly true for chemotherapeutic agents that potentially have highly toxic effects on non-target tissues. For instance, most anti-cancer chemotherapeutic agents function by selectively poisoning replicating cells. This mechanism inevitably targets the rapidly replicating cells, such as those of the bone marrow that generate a number of important blood cells. If the biodistribution of the chemotherapeutic drug is changed so that useful concentrations are maintained in the cancerous tissue or the tissue in which the cancer resides while concentrations distal from the cancer situs are reduced, the scope of toxic side effects will generally be reduced.

Additionally, since cancer, antimicrobial and other biological agents exhibit toxicities, it would be beneficial if dosages were lowered without adversely affecting the therapeutic index.

Tumors of the central nervous system present a particularly difficult therapeutic challenge. Such tumors are often difficult to surgically excise and surgical excision can have unacceptable consequences. These tumors can be difficult to treat with radiation since they are sometimes difficult to precisely locate and are often too close to tissues that are critical to the well-being of the tumor patient. Such tumors cannot be effectively treated by standard chemotherapies since the fraction of the administered chemotherapeutic agent that will reach the tumor is very small. The effective dosage at the tumor cannot be increased by administering higher dosages to the patient, since standard dosages are generally close to the dose that cause unacceptable side effects.

Cytokines

Cytokines are polypeptides secreted by cells. Cytokines play an important role in the interactions between cells in the immune system, and are therefore potentially effective drugs for the treatment of cancer, as well as viral-related and other diseases. The mechanism of action of these protein factors is connected with specific activation of the immune system which, in turn, protects against many pathological processes. Well known are antiviral preparations on the-basis of interferons (Infs) that are already used in clinical practice. For example, clinical tests of interleukin-2 (IL-2) and tumor necrosis factor (TNF) as anticancer drugs have yielded promising results. A great deal of work has been devoted to creation of new drugs on the basis of IL-4 and other lymphokines.

Generally speaking, recombinant cytokines possess low affinity for specific receptors on target cells because of incorrectly formed tertiary structures and the absence of necessary post-translational modifications in bacterial superproducers. Such recombinant preparations display low biological activity, and very high doses are required, producing considerable side effects.

Hormones

Hormones are chemical messenger molecules secreted by endocrine glands which regulate various aspects of metabolism. Insulin, for example, is a protein hormone secreted in the pancreas by the islets of Langerhans. Insulin stimulates catabolism of glucose and blocks glycogenolysis, thereby facilitating diffusion of glucose into most cells. The inability to form insulin results in diabetes mellitus, which is currently treated through insulin injection in conjunction with dietary regulation to control blood sugar levels. Insulin production and thus is of particular interest in molecular biology and enzymology.

It is therefore desirable to administer a biological agent or agents to a patient in a composition which can be administered orally, and which alleviates some or all of the above difficulties.

SUMMARY OF THE INVENTION

The present invention thus relates to compositions for oral administration comprising a biological agent and a block copolymer.

In one embodiment, the invention provides a pharmaceutical composition comprising:
(a) a biological agent;
(b) a polyether block copolymer comprising an A-type linear polymeric segment joined at one end to a B-type linear polymeric segment, wherein the A-type segment is of relatively hydrophilic character, the repeating units of which have molecular weight contributions between about 30 and about 500, wherein the B-type segment is of relatively hydrophobic character, the repeating units of which have molecular weight contributions between about 30 and about 500, wherein at least about 80% of the linkages joining the repeating units for each of the polymeric segments comprise an ether linkage; and
(c) a targeting moiety coupled to a lipophilic moiety comprising a hydrocarbon having from about 3 to about 41 carbon atoms, more preferably a hydrocarbon having from about 5 to about 25 carbon atoms, and more preferably, a hydrocarbon having from about 9 to about 17 carbon atoms.

The invention thus relates to pharmaceutical compositions comprising a biological agent and a poly(oxyethylene)-poly(oxypropylene) block copolymer. Preferred compositions include those wherein the poly(oxypropylene) [i.e., hydrophobe] portion of said block copolymer comprises at least 50% by weight of the block copolymer. Also preferred are compositions wherein the hydrophobe molecular weight of the block copolymer is at least about 900, and more preferably at least about 1700. Especially preferred are compositions wherein the hydrophobe molecular weight of the polyether block copolymer is at least about 2000 and the hydrophobe weight percentage is at least about 20%. The invention also relates to methods of treatment using the same.

Also preferred are compositions wherein the block copolymers have a critical micellar concentration ("CMC") of about 0.5% wt/vol. or less at 37° C. in an isotonic aqueous solution.

In yet another preferred embodiment, the polyether block copolymer is selected from the group consisting of polymers of formulas:

wherein A and A' are A-type linear polymeric segments, B and B' are B-type linear polymeric segments, and $R^1$, $R^2$, $R^3$ and $R^4$ are either block copolymers of formulas (I), (II) or (III) or hydrogen and L is a linking group, with the proviso that no more than two of $R^1$, $R^2$, $R^3$ or $R^4$ is be hydrogen.

In a preferred embodiment, the composition is adapted to include micelles composed of the block copolymer or to form micelles composed of the block copolymers during the course of administration or subsequent thereto. Preferably, at least about 0.1% of the biological agent is incorporated in the micelles, more preferably, at least about 1.0% of the biological agent, yet more preferably, at least about 5% of the biological agent.

In a preferred embodiment, the hydrophobe percentage of the copolymer of the composition is at least about 50% more preferably, at least about 60%, yet more preferably 70%.

In another preferred embodiment, the hydrophobe weight of the copolymer is at least about 900, more preferably, at least about 1700, yet more preferably at least about 2000, still more preferably at least about 2300.

In further preferred embodiments, the hydrophobe weight is at least about 2000 and the hydrophobe percentage is at least about 20%, preferably 35%; or the hydrophobe weight is at least about 2300 and the hydrophobe percentage is at least about 20%, preferably 35%.

In another preferred embodiment, the copolymer or copolymers of the composition have a critical micellar concentration ("CMC") of no more than about 0.5% wt/vol. at 37° C. in an isotonic aqueous solution, preferably, no more than about 0.05% wt/vol., more preferably, no more than about 0.01% wt/vol., yet more preferably, no more than about 0.003% wt/vol.

Preferably, the copolymers of the composition conform to Formula (V), which is set forth in the text below. Particularly preferred among these copolymers are those having hydrophobe weights between about 1500 and about 2000, preferably between about 1710 and about 1780, and hydrophobe percentages between about 85% and about 95%, preferably between about 88% and about 92%. Also particularly preferred among these copolymers are those having hydrophobe weights between about 3000 and about 3500, preferably between about 3200 and about 3300, and hydrophobe percentages between about 15% and about 25%, preferably between about 18% and about 22%. Additionally particularly preferred among these polymers are that having hydrophobe weights between about 3500 and about 4000, preferably between about 3700 and about 3800, and hydrophobe percentages between about 25% and about 35%, preferably between about 28% and about 32%.

In a preferred embodiment, the biological agent of the composition is an agent that affects the function of the brain or treats or prevents a disease of the brain.

In a second embodiment, the invention provides a pharmaceutical composition comprising an biological agent solubilized in polymeric micelles having associated therewith a targeting moiety coupled to a lipophilic moiety comprising hydrocarbon having from about 3 to about 41 carbon atoms, more preferably a hydrocarbon having from about 5 to about 25 carbon atoms, yet more preferably, a hydrocarbon having from about 9 to about 17 carbon atoms.

In another embodiment, the invention provides a method of targeting a biological agent to a pre-selected tissue. The method comprises administering the composition described above, wherein the targeting moiety is selected to target the tissue, to an animal having the pre-selected tissue.

In yet another embodiment, the invention provides a method of treating a microbial disease or a tumor of the brain by administering a composition comprising:

(a) a chemotherapeutic agent; and (b) a polyether block copolymer comprising an A-type linear polymeric segment joined at one end to a B-type linear polymeric segment, wherein the A-type segment is of relatively hydrophilic character, the repeating units of which contribute an average Hansch-Leo fragmental constant of about 0.4 or less and have molecular weight contributions between about 30 and about 500, wherein the B-type segment is of relatively hydrophobic character, the repeating units of which contribute an average Hansch-Leo fragmental constant of about –0.4 or more and have molecular weight contributions between about 30 and about 500, wherein at least about 80% of the linkages joining the repeating units for each of the polymeric segments comprise an ether linkage. In a preferred embodiment, the composition used in this embodiment will include a targeting molecule.

In yet another embodiment, the invention relates to compositions for the delivery of biologically active agents comprising a poly(oxyethylene)-poly(oxypropylene) block copolymer and at least one of (a) a protein, peptide, or derivative thereof, or (b) a biologically active agent, or derivative thereof having reduced cellular transport, reduced penetration into tissues, or reduced penetration across biological barriers, due to membrane proteins, wherein the hydrophobe percentage of the poly(oxyethylene)-poly(oxypropylene) block copolymer is at least about 50%.

The preferred block copolymers are of the formula:

$$HO-[CH_2CH_2O]_x-[CHCH_2O]_y-[CH_2CH_2O]_z-H;$$
with $CH_3$ on middle block $$HO-[CH_2CH_2O]_x-[CHCH_2O]_y-H;$$
with $CH_3$ $$HO-[CHCH_2O]_x-[CH_2CH_2O]_y-[CHCH_2O]_z-H;$$
with $CH_3$ groups

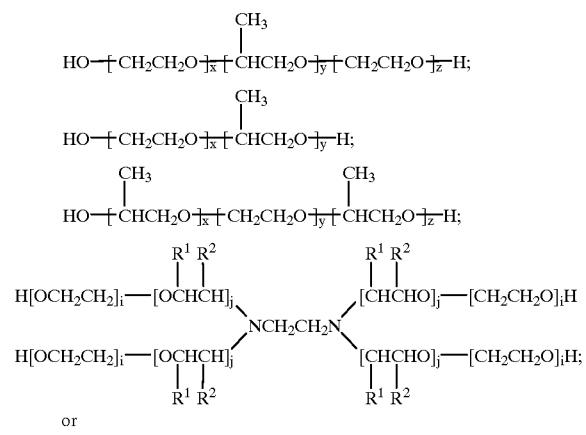

or

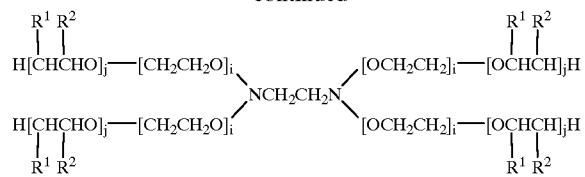

in which x, y, z, i, and j have values from about 2 to about 800, and wherein for each $R^1$, $R^2$ pair, one is hydrogen and the other is a methyl group.

In another preferred embodiment, the invention relates to compositions for the delivery of a biologically active agent, or derivative thereof, comprising a biologically active agent, or derivative thereof, and a POE-POP block copolymer of the formula:

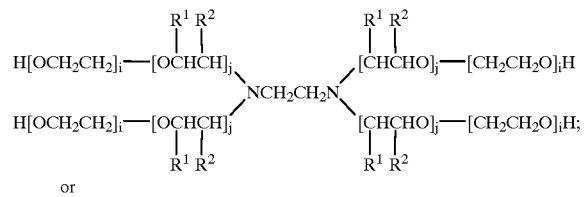

or

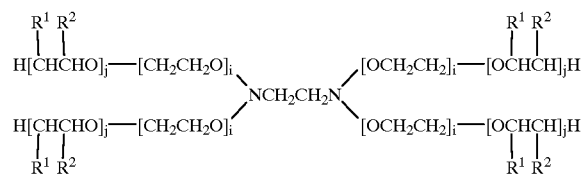

wherein for each $R^1$, $R^2$ pair, one is hydrogen and the other is a methyl group.

In yet another preferred embodiment, the invention relates to compositions for the delivery of a biologically active agent, or derivative thereof comprising a biologically active agent, or derivative thereof, and a POE-POP block copolymer of the formula:

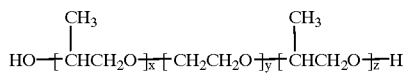

in which x, y, and z have values from about 2 to about 800.

In still another preferred embodiment, the invention relates to compositions comprising at least one block copolymer with ethylene(oxide) content of 50% or less, and at least one block copolymer with ethylene(oxide) content of 50% or more, and a biologically active agent. The ratio by weight of the block copolymer with ethylene(oxide) content of 50% or less to the block copolymer with ethylene(oxide) content of 50% or more is 1:2, more preferably 1:5.

The protein, peptide or derivative thereof may be preferably, for example, an immunomodulator, cytokine, hormone, enzyme, tissue plasminogen activator, clotting factor, colony stimulating factor, neuropeptide, recombinant soluble receptor, monoclonal antibody, or erythropoietin. Preferred hormones include human growth hormone, and insulin.

The invention also relates to methods of treating a mammal using these compositions.

The invention also relates to compositions for oral delivery which comprise mixtures of at least one block copolymer with ethylene(oxide) content of less than 50% (i.e., hydrophobic copolymer), and at least one block copolymer with ethylene(oxide) content of more than 50% ((i.e., hydrophilic copolymer). Preferably, these will be in a ratio of 2 hydrophilic copolymers to 1 hydrophobic copolymer, and more preferably in a ratio of 5 hydrophilic copolymers to 1 hydrophobic copolymer, and even more preferably in a ratio of 10 hydrophilic copolymers to 1 hydrophobic copolymer.

DETAILED DESCRIPTION OF THE INVENTION

Definitions

Figure 1A:
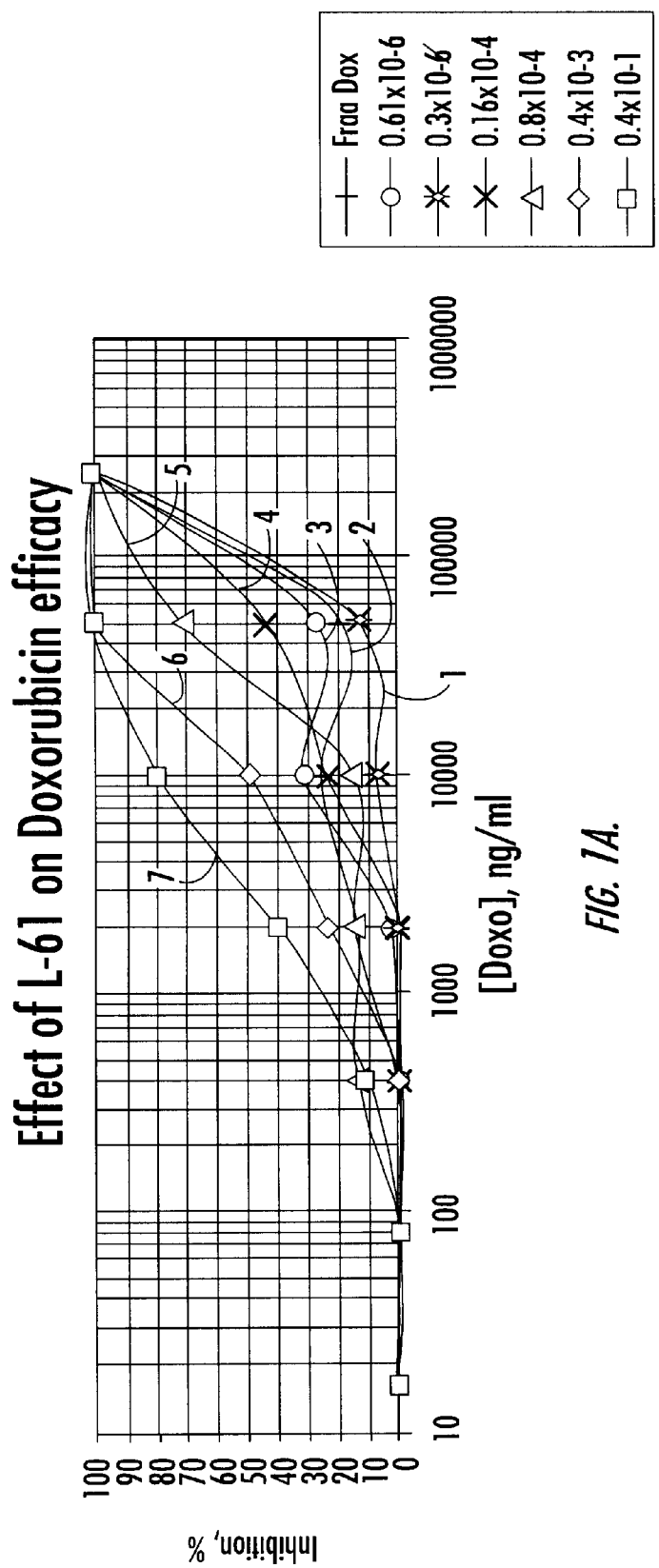
FIGS. 1A and 1B show the inhibition of doxorubicin-resistant MCF7 cells incubated with various concentrations of doxorubicin and Pluronic L61.

The terms or phrases listed below shall have the following meaning:

Biological agent: An agent that is useful for diagnosing or imaging or that can act on a cell, organ or organism, including but not limited to drugs (pharmaceuticals) to create a change in the functioning of the cell, organ or organism. Such agents can include but are not limited to peptides and polypeptides, nucleic acids, polynucleotides, antibacterial agents, antiviral agents, antifungal agents, anti-parasitic agents, tumoricidal or anti-cancer agents, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-inflammatories, anti-glaucomic agents, mydriatic compounds and local anesthetics, and biological agents that act on cells of the central nervous system or diseases of the central nervous system.

Central nervous system agents: Biological agents that act on cells of the central nervous system or diseases of the central nervous system.

Chemotherapeutic agent: A biological agent that inhibits the growth or decreases the survival of neoplastic or pathogenic microbial cells or inhibits the propagation (which includes without limitation replication, viral assembly or cellular infection) of a virus.

Hydrophobe percentage: The percentage of the molecular weight of a block copolymer that is made up of B-type blocks.

Hydrophobe weight: The molecular weight contribution of the B-type blocks of a block copolymer.

$IC_{50}$: The concentration at which 50% cytotoxicity is obtained. Cytotoxicity can be measured by the method of Alley et al., Cancer Res. 48: 589–601, 1988 or Scudiero el al., Cancer Res., 48:4827, 1988. In particular, it can be measured based on the drug concentration at which a 50% reduction in the activity of mitochondrial enzymes is observed.

$IC_{95}$: The concentration at which 95% cytotoxicity is obtained. Cytotoxicity can be measured by the method of Alley et al., or Scudiero et al., above. In particular, it can be measured based on the drug concentration at which a 95% reduction in the activity of mitochondrial enzymes is observed.

Lipophilic moiety: A lipophilic substituent that is joined to a targeting moiety and that partitions into the lipophilic portion of copolymer micelles.

Microbe: A bacteria, mycoplasma, yeast or fungi, virus or parasite (such as a malaria parasite).

MDR: The phenomenon of simultaneous resistance to unrelated biological agents.

Targeting moiety: A molecular structure that is recognized by a cellular, tissue, viral or substratum component such as a cell surface receptor or acceptor molecule.

It will be understood that the copolymer characteristics described below are suitable for the oral delivery of the compositions of both the targeting embodiments of the invention and the brain chemotherapy embodiments of the invention.

The present invention relates among other things to pharmaceutical compositions and methods for biological agents particularly those, whose target cells or tissues are resistant to the biological agent. Multidrug resistance (MDR) describes the phenomenon of simultaneous resistance to unrelated biological agents. It has been associated with overexpression of membrane proteins belonging to the superfamily of the ATP-binding cassette (ABC) proteins. See Ling, Cancer Chemother. Pharmacol., 40 Suppl: S3–S8 (1997); Brown et al., Proc. Natl. Acad. Sci., USA, 92: 5421–5425 (1995). ABC/MDR related proteins, such as glycoprotein P (P-gp), P-gp-related protein (PRP), ABC/MDR-associated protein (MRP), and lung resistance-related protein (LRP), have been identified in a variety of prokaryotic and eukaryotic cells. See Den-Boer et al., Leukemia 11:1078–1085 (1997); Davey et al., Leuk. Res., 20: 657–664 (1996); Furuya et al., Leuk. Res. 20: 657–664 (1996). Furuya et al, Cancer-Res. 57: 3708–3716 (1997). It Is believed that human gene contains a minimum of 200 ABC transporter superfamily members. See Ling Cancer Chemother. Pharmacol, 40 Supp.: S3–S8 (1997). Members of the glycoprotein P family of membrane proteins are believed to be responsible for the multidrug resistance of many of the tumors whose resistance can be reversed using the composition of the invention. See Goldstein et al., Cancer treatment Res., 57: 101–119 (1991). These proteins are believed to function as pumps that export the biological agent against which the tumors have become resistant. Members of the same protein family are believed to reside in the membranes of the endothelial calls lining blood vessels in the brain and to be responsible for the "blood-brain barrier" (BBB) function that excludes effective amounts of many biological agents from entering the brain. See for example, Tatsauta et al., J. Biol. Chem. 267: 2038320391.

Compositions of the present invention can be used to enhance drug permeability into the brain, as discussed in more detail in U.S. application Ser. No. 08/478,979 filed Jun. 7, 1995 and entitled "Compositions for Targeting Biological Agents", the contents of which are incorporated herein by reference. Members of this protein family are believed also to control the permeability of intestinal epithelium cells with respect to numerous biological agents (Thiebault et al, Proc. Nail. Acad. Sci., USA, 84: 7735 (1987), including peptides (Nerurkar et al., Pharm. Res., 13: 528 (1996). Further, members of this protein family are believed to be responsible for drug resistance in certain Candida, malaria and other microbial Infections. Overexpression of the human MRP causes a form of multidrug resistance similar to that conferred by glycoprotein-P. MRP is believed to be a primary active transporter of a structurally diverse range of organic anionic conjugates. A variety of chemosensitizing agents have been described that can interfere with glycoprotein-P and MRP function and it is believed that such agents may improve the efficacy of conventional therapy when used in combination with such regimens. See Linn Cancer *Chemother. Pharmacol.*, 40 Suppl: S3–S8 (1997).

Without wishing to be bound to a particular theory, it is believed that the compositions of the invention reverse efflux mechanisms mediated by members of the glycoprotein-P family and other drug resistance mechanisms, particularly (but not limited to) those associated with overexpression of ABC/MDR-related proteins. This results in improved performance of the biological agents, including but not limited to improved delivery of the biological agents to a target cell or tissue, increased permeability of the biological barriers separating such target cells and tissues, and inhibition of mechanisms eliminating the biological agents from the target cells or tissue, in one specific embodiment the current invention provides for the compositions for improved oral bioavailability of biological agents that are affected by ABC/MDR-related membrane proteins. In another specific embodiment the current invention provides for the improved brain delivery of such biological agents, in another embodiment the current invention provides for the improved compositions of biological agents having decreased cellular accumulation as a result of mechanisms associated with ABC/MDR-related membrane proteins. In yet another specific embodiment the current invention provides for improved chemotherapeutic compositions effective against MDR cancers. In yet another specific embodiment the current invention provides for improved chemotherapeutic compositions for treatment of brain tumors. In yet another specific embodiment the current invention provides for improved compositions for CNS agents.

Recent observations described in more detail in U.S. application Ser. No. 08/478,978 filed Jun. 7, 1995, entitled "Biological Agent Compositions", the contents of which are incorporated herein, demonstrate the effectiveness of the block copolymers of the invention in enhancing the potency of chemotherapeutic drugs and reversing drug resistance is highly dependent (a) on the hydrophobe percentage and (b) on the hydrophobe weight. The effectiveness increases with either an increase in the percentage (a) or an increase in weight (b), or both. These hydrophobe percentage and hydrophobe weight increases also correlate with improved micelle formation properties wherein micelle formation for these copolymers occurs at lower concentrations. See, Hunter et al., *Macromolecules* 26: 5030 (1993); Hunter et. al., *Macromolecules* 26: 5592 (1993); Alexandris et. al., *Macromolecules* 27: 2414 (1994).

While not wishing to be limited to a particular theory, it is believed that micelle formation serves as a surrogate for measuring the physical properties that lead to improved biological agent delivery properties. Again, not wishing to be limited to a particular theory, it is believed that it is not micelles per se that lead to improved biological agent efficiency and reversion of multidrug resistance.

The multidrug resistant cell line which expresses high levels of glycoprotein P (Gervasoni, el al., *Cancer Research*, 51, 4955 (1991) can be used to evaluate the effects of the block copolymers on biological active agents. MDR drums such as daunorubicin or rhodamine 123 can serve as probes for the effects on the membrane proteins associated with MDR in cancer and normal cells (Jancis, et al., *Mol. Pharmacol.*, 43, 51 (1993); Lee, et al., *Mol. Pharmacol.*, 46, 627 (1994). The results with these probes are indicative of the effects on the transport of all MDR class drugs.

If, using doxorubicin as a model biological agent, the ratio of (a) the $IC_{50}$ (a measure of effective cytotoxicity concentration) for a copolymer-containing composition to (b) the $IC_{50}$ for free doxorubicin is plotted against the concentration of copolymer, the plot is biphasic, with a rapid decrease in the ratio seen as copolymer concentrations increase but remain under the CMC of the copolymer. Above the CMC, a rapid leveling off of the ratio is observed. Maximal enhancement of biological agent activity occurs above the CMC, although enhancement activity is seen at concentrations, for the copolymer Pluronic L61, as low as 0.0001% wt/vol., or less. The micellar form is also believed to be important to using the copolymers in drug delivery for other reasons, as will be discussed below.

The schematic below is helpful in understanding the relationship between the hydrophobe percentage and the hydrophobe weight of a copolymer and various aspects of the present invention. In the schematic, the weight of the hydrophobe (poly(oxypropylene)) and of the copolymer are shown directly under each identified copolymer. Adjacent to these values are the hydrophobe percentage values for each copolymer.

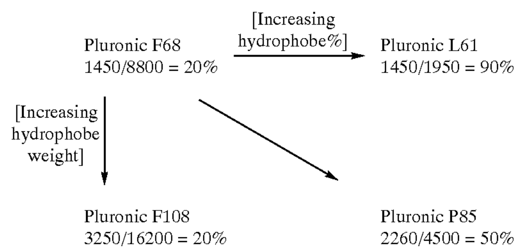

Pluronic F68 has been determined to have only a modest activity in enhancing the potency of biological agents. Pluronic L61, which has the same hydrophobe weight as Pluronic F68 but a much higher hydrophobe percentage, is generally the most effective of the block copolymers identified in the schematic. Pluronic F108, which has the same hydrophobe percentage as Pluronic F68 but a much higher hydrophobe weight, is also an effective copolymer, though much less effective than Pluronic L61. Pluronic P85 has a greater hydrophobe weight and a greater hydrophobe percentage than Pluronic F68, but the difference in each value is less than it is for Pluronics F108 and L61, respectively. The effectiveness of Pluronic P85 in enhancing the potency of biological agents is intermediate between the effectiveness of Pluronic F108 and of Pluronic L61. These differences in effectiveness are exemplified when various copolymers, at a concentration above CMC, and doxorubicin are incubated in vitro with drug resistant cells. The ratio of the IC50 value for doxorubicin in the absence of copolymer to the ratio in the presence of copolymer is the "resistance reversion index." The resistance reversion index values for various copolymers are:

| Doxorubicin formulation | $IC_{50}$, ng/ml | Resistance reversion index |
|---|---|---|
| free drug | 60,000 | n.a. |
| +5% (w/v) Pluronic F68 | 60,000 | 1 |
| 0.01% (w/v) Pluronic F108 | 10,000 | 6 |
| 0.01% (w/v) Pluronic P85 | 2,000 | 30 |
| 0.01% (w/v) Pluronic L61 | 60 | 1000 |

The importance of the micellar form in delivering biological agents is also revealed in in vivo experiments. In the micellar form, biological agents are located in the hydrophobic core of the micelles, thereby masked by the hydrophilic shell (composed of A-type segments) surrounding the micelles. This masking decreases interactions with liver, plasma proteins, other non-target tissues and other molecules that can bind or inactivate the agent or convert the agent to a toxic metabolite. For example, rapid metabolism of anthracycline antibiotics by the liver leads to the formation of cardiotoxic metabolites that are modified at the C13 position. See, Mushlin, et al., *Br. J. Pharmacol.*, 110: 975–982 (1993). Using doxorubicin as a model drug, the micellar form decreases liver uptake, decreases conversion to doxorubicinol, and decreases the rate at which the concentration of doxorubicin in the blood decreases.

The effectiveness of copolymers in (a) forming micelles (where greater effectiveness is measured in reduced CMCS) and (b) favoring the partitioning of various biological agents to the micellar rather than the free form of various biological agents increases according to the same pattern. Thus, the hierarchy of effectiveness is again L61>P85>F108>>F68. The presence of micelles at low concentrations is believed to help assure, assuming that biological agent remains associated with the micelles, that the biological agent and the copolymer arrive together at a target tissue. Partitioning coefficients that favor the micellar form help assure that the assumption that the biological agent remains associated with micelles will hold true. The micellar form of the biological agent is also believed to protect the biological agent from uptake by non-target tissues, which tissues may metabolize the biological agent into an ineffective or toxic metabolite, and non-specific adsorption to blood components, cellular components and the like.

At high concentrations, block copolymers can be toxic to the liver, kidney or other cells of a subject. See, BASF Corp., Pluronic Material Safety Data Sheet and Drug Master Files. The toxicity of block copolymers increases with the hydrophobicity parameters of block copolymers according to the same pattern seen for increases in effectiveness in potentiating biological agents. Fortunately, the rate of increase in potency as these hydrophobicity parameters change is much greater than the increase in copolymer toxicity. For instance, as illustrated in Example 20, the $LD_{50}$ of L61 in BALB/c mice is 10-fold lower than the $LD_{50}$ of Pluronic F108. However, the difference in the optimal therapeutic dose is more than 100-fold improved for Pluronic L61 vs. Pluronic F108. (See Example 14.) Thus, the concentration range over which effectiveness in potentiating the activity of a biological agent can be maintained while avoiding toxicity due to copolymer is increased for Pluronic L61 vs. Pluronic F108.

The compositions of the invention are intended to include either preformed micelles with a substantial portion of the biological agent incorporated therein, or copolymer compositions which form micelles with a substantial portion of the agent dissolved therein during the course of the administration of the biological agent to a patient, or subsequent thereto. For the targeting embodiment of the invention, the targeting moiety will either be pre-associated with micelles or will associate with micelles during the course of administration. Particularly preferred block copolymers are those that have low CMC values in isotonic solutions at physiological temperatures. Such block copolymers will maintain a micellar delivery vehicle for biological agents even after substantial dilution into a physiological fluid such as a treatment subject's blood. Such low CMC values allow for the use of reduced levels of block copolymers in the drug composition of the invention.

The invention is described below with reference to the fragmental constants developed by Hansch and Leo. See Hansch and Leo, *Substituent Constants for Correlation Analysis in Chemistry and Biology*, Wiley, New York, 1979; James, *Soluhility and Related Properties*, Marcel Dekker, New York, 1986, pp. 320–325. These constants were developed for use in estimating the contribution of a portion of a molecule to the tendency of the molecule to partition between the phases formed by octanol-water mixtures. These constants are generally referred to as Hansch-Leo fragmental partition constants (hereinafter "Hansch-Leo fragmental constants").

The entire disclosure of U.S. application Ser. No. 08/478,978 filed Jun. 7, 1995, entitled, "Biological Agent Compositions", filed on Jun. 7, 1995 is incorporated herein by reference, as is the entire disclosure of U.S. patent application Ser. No. 08/054,403, filed Apr. 28, 1993.

The number of repeating units of the total hydrophilic (A-type) blocks or the total hydrophobic (B-type) blocks for a polyether copolymer are preferably between about 2 and about 800. More preferably, the number of repeating units is between about 4 and about 200, still more preferably, between about 5 and about 80. The repeating units that comprise the blocks, for A-type and B-type blocks, will generally have molecular weight between about 30 and about 500, preferably between about 30 and about 100, still more preferably between about 30 and about 60. Generally, in each of the A-type or B-type blocks, at least about 80% of the linkages between repeating units will be ether linkages, preferably, at least about 90% will be ether linkages, more preferably, at least about 95% will be ether linkages. Ether linkages, for the purposes of this application, encompass glycosidic linkages (i.e., sugar linkages). However, in one aspect, simple ether linkages are preferred.

Preferably, all of the repeating units that comprise A-type blocks have a Hansch-Leo fragmental constant of less than about −0.4, more preferably, less than about −0.5, still more preferably, less than about −0.7. Preferably, all of the repeating units that comprise B-type blocks have a Hansch-Leo fragmental constant of about −0.30 or more, more preferably about −0.20 or more.

Polymers according to the first embodiment of the invention are exemplified by the block copolymers having the formulas:

(V)

(VI)

(VII)

(VIII)

or

-continued

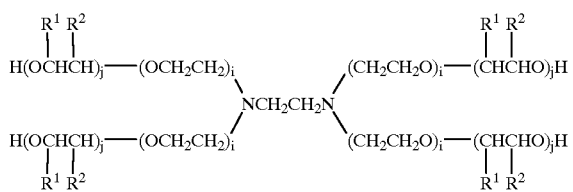

(VIV)

in which x, y, z, i, and j have values from about 2 to about 800, preferably from about 5 to about 200, more preferably from about 5 to about 80, and wherein for each $R^1$, $R^2$ pair, one is hydrogen and the other is a methyl group. Formulas (V) through (VII) are oversimplified in that, in practice, the orientation of the isopropylene radicals within the B block will be random. This random orientation is indicated in formulas (VIII) and (VIV), which are more complete. Such poly(oxyethylene)poly(oxypropylene) compounds have been described by Santon, *Am. Perfumer Cosmet.*, 72(4) :54–58 (1958); Schmolka, Loc. cit. 82(7):25–30 (1967), *Non-ionic Suifactants*, Schick, ed. (Dekker, N.Y., 1967), pp. 300–371. A number of such compounds are commercially available under such generic trade names as "lipoloxamers", "pluronics" and "synperonics." Pluronic polymers within the B-A-B formula are often referred to as "reversed" pluronics, "pluronic R" or "meroxapol."

The "polyoxamine" polymer of formula (VIII) is available from BASF (Wyandotte, Mich.) under the tradename Tetronic™. The order of the polyoxyethylene and polyoxypropylene blocks represented in formula (VIII) can be reversed, creating Tetronic R™, also available from BASF. See, Schmolka, *J. Am. Oil. Soc.*, 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename Pluradot™.

The hydrophobic/hydrophilic properties of a given block copolymer depends upon the ratio of the number of oxypropylene groups to the number of oxypropylene groups. For a composition containing a single block copolymer of poly(oxyethylene)-poly(oxypropylene), for example, this relationship, taking into account the molecular masses of the central hydrophobic block and the terminal hydrophilic blocks, can be expressed as follows:

$$n = \frac{H}{L} \cdot 1.32$$

in which H is the number of oxypropylene units and L is the number of oxyethylene units. In the general case of a block copolymer containing hydrophobic B-type segments and hydrophilic A-type segments, the hydrophobic-hydrophilic properties and micelle-forming properties are related to the value n as defined as:

$$n=(|B|/|A|)\times(b/a)$$

where |B| and |A| are the number of repeating units in the hydrophobic and hydrophilic blocks of the copolymer, respectively, and b and a are the molecular weights for the respective repeating units.

Selecting a block copolymer with the appropriate n value depends upon the hydrophobic/hydrophilic properties of the specific agent, or the composite hydrophilic/hydrophilic properties of a mixture of agents to be formulated. Typically, n will range in value from about 0.2 to about 9.0, more preferably between about 0.25 and about 1.5. This range should be viewed not as numerically critical but as expressing the optimum hydrophobic/hydrophilic balance between the predominantly hydrophilic poly(oxyethylene) blocks, and the predominantly hydrophobic poly(oxypropylene) blocks.

An important aspect of the present invention-involves utilizing mixture of different block-copolymers of poly(oxyethylene)-poly(oxypropylene) to achieve a more specific hydrophobic-hydrophilic balance suitable for a given cytokine or mixture of several cytokines, preserving the optimal size of particles. For example, a first block copolymer may have an n of 1.0 whereas a second may have a value of 1.5. If material having an n of 1.3 is desired, a mixture of one weight portion of the first block copolymer and 1.5 weight portion of the second block-copolymer can be employed.

Thus, a more generalized relationship for such mixtures can be expressed as follows:

$$N = 1.32 \cdot \left[ \frac{H_1 \cdot m_1}{(L_1) \cdot (m_1 + m_2)} + \frac{H_2 \cdot m_2}{(L_2) \cdot (m_1 + m_2)} \right]$$

in which $H_1$ and $H_2$ are the number of oxypropylene units in the first and second block copolymers, respectively; $L_1$ is the number of oxyethylene units in the first block copolymer; $L_2$ is the number of oxyethylene units in the second block copolymer; $m_1$ is the weight proportion in the first block-copolymer; and $m_2$ is the weight proportion in the second block copolymer.

An even more general case of a mixture of K block copolymers containing hydrophobic B-type block copolymers and hydrophilic A-type block copolymers, the N value can be expressed as follows:

$$N = \frac{b}{a} \sum_{i=1}^{k} \left( \frac{|B|_i}{|A|_i}, \frac{m_i}{M} \right)$$

where $|A|_i$ and $|B|_i$ are the numbers of repeating units in the hydrophilic (A-type) and hydrophobic (B-type) blocks of the i-th block copolymer, m is the weight proportion of this block copolymers, M is the sum of weight proportions of all block copolymers in the mixture $$\left( M = \sum_{i=1}^{k} m_i \right),$$

and a and b are the molecular weights for the repeating units of the hydrophilic and hydrophobic blocks of these block copolymers respectively.

If only one block copolymer of poly(oxyethylene)-poly(oxypropylene) is utilized, N will equal n. An analogous relationship will apply to compositions employing more than two block copolymers of poly(oxyethylene)-poly(oxypropylene).

Where mixtures of block copolymers are used, a value N will be used, which value will be the weighted average of n for each contributing copolymers, with the averaging based on the weight portions of the component copolymers. The value N can be used to estimate the micelle-forming properties of a mixture of copolymers. The use of the mixtures of block copolymers enhances solubility and prevents aggregation of more hydrophobic block copolymers in the presence of the serum proteins. Particularly, poly(oxyethylene)-poly(oxypropylene) block copolymers with the ethylene oxide content of more than 50% solubilize hydrophobic block copolymers with ethylene oxide content of no more than 50%. In such mixtures, the preferred ratio of the hydrophilic and hydrophobic copolymer is at least 2:1 (w/w), preferably at least 5:1 (w/w), still more preferably at least 8:1 (w/w)." When copolymers other than polyethylene oxide-polypropylene oxide copolymers are used, similar approaches can be developed to relate the hydrophobic/hydrophilic properties of one member of the class of polymers to the properties of another member of the class.

Using the above parameters, one or more block copolymers of poly(oxyethylene)-poly(oxypropylene) are combined so as to have a value for N of from about 0.1 to about 9, more preferably from about 0.25 to about 1.5. The combined copolymers form micelles, the value of N affecting in part the size of the micelles thus produced. Typically the micelles will have an average diameter of from about 10 to about 25 nm, although this range can vary widely. The average diameter of any given preparation can be readily determined by quasi-elastic light scattering techniques.

For more effective solubilization of some cytokines, for example, their point modification with fatty acid residues that act as hydrophobic anchors during incorporation of such agents into block copolymer micelles is required. For some cytokines, the incorporation into the micelles formed by the block-copolymer is achieved through the covalent conjugation of the cytokine and block copolymer. Various methods of such conjugation are used. These include cross-linking of the drug directly to an activated terminal group of a block copolymer of conjugation via a spacer groups using various heterobifunctional agents.

A number of pluronics are designed to meet the following formula:

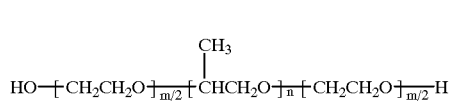

(IX)

Of course, the ordinarily skilled artisan will recognize that the values of m and n will usually represent a statistical average and that the number of repeating units of the first block of a given molecule will generally not be exactly the number of repeating units of the third block. The characteristics of a number of pluronics, described with reference to formula (IX), are as follows:

| Copolymer | Hydrophobe weight | CMC (% w/v) | Hydrophobe percentage |
|---|---|---|---|
| Pluronic L61 | 1750 | 0.0003 | 90 |
| Pluronic L64 | 1750 | 0.002 | 60 |
| Pluronic F68 | 1750 | 4–5 | 20 |
| Pluronic P85 | 2250 | 0.005–0.007 | 50 |
| Pluronic F127 | 4000 | 0.003–0.005 | 30 |
| Pluronic F108 | 3250 | 0.0035–0.007 | 20 |

These CMC values were determined by the surface tension method described in Kabanov et al., *Macromolecules* 28: 2303–2314 (1995).

Additional specific poly(oxyethylene)-poly(oxypropylene) block copolymers relevant to the invention include:

| Pluronic | Hydrophobe Weight | Hydrophobe Percentage |
|---|---|---|
| L31 | 950 | 90% |
| F35 | 950 | 50% |
| L42 | 1200 | 80% |
| L43 | 1200 | 70% |
| L44 | 1200 | 60% |
| L61 | 1750 | 90% |
| L62 | 1750 | 80% |
| L63 | 1750 | 70% |
| P65 | 1750 | 50% |
| F68 | 1750 | 20% |
| L72 | 2050 | 80% |
| P75 | 2050 | 50% |
| L81 | 2250 | 90% |
| P84 | 2250 | 60% |
| P85 | 2250 | 50% |
| F87 | 2250 | 30% |
| F88 | 2250 | 20% |
| L92 | 2750 | 80% |
| F98 | 2750 | 20% |
| P103 | 3250 | 70% |
| P104 | 3250 | 60% |
| P105 | 3250 | 50% |
| F108 | 3250 | 20% |
| L121 | 4000 | 90% |
| L122 | 4000 | 80% |
| L123 | 4000 | 70% |
| F127 | 4000 | 30% |
| 10R5 | 1000 | 50% |
| 10R8 | 1000 | 20% |
| 12R3 | 1200 | 70% |
| 17R2 | 1700 | 80% |
| 17R2 | 1700 | 80% |
| 17R4 | 1700 | 60% |
| 17R8 | 1700 | 20% |
| 22R4 | 2200 | 60% |
| 25R1 | 2500 | 90% |
| 25R2 | 2500 | 80% |
| 25R4 | 2500 | 60% |
| 25R5 | 2500 | 50% |
| 25R8 | 2500 | 50% |
| 31R1 | 3100 | 90% |
| 31R2 | 3100 | 80% |
| 31R4 | 3100 | 60% |

*All copolymers above this conform to formula (IX), this copolymer and those below conform to formula (VII).

The diamine-linked pluronic of formula (VIII) can also be a member of the family of diamine-linked polyoxyethylene-polyoxypropylene polymers of formula:

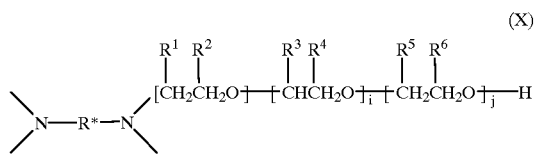

(X)

wherein the dashed lines represent symmetrical copies of the polyether extending off the second nitrogen, R* an alkylene of about 2 to about 6 carbons, a cycloalkylene of about 5 to about 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen. The $-NH_2-CH_2CH_2-NH_2-$ group of formula (VIII) and the $N-R^*-N$ group of formula (X) are examples of linking groups, L, of formula (IV).

Those of ordinary skill in the art will recognize that even when the practice of the invention is confined for example, to poly(oxyethylene)-poly(oxypropylene) compounds, the above exemplary formulas are too confining. An important feature is that the average Hansch-Leo fragmental constant of the monomers in an A-type block be about −0.4 or less. Thus, the units making up the first block need not consist solely of ethylene oxide. Similarly, not all of the B-type block need consist solely of propylene oxide units. Instead, the blocks can incorporate monomers other than those defined in formulas (V)–(X), so long as the parameters of the first embodiment are maintained. Thus, in the simplest of examples, at least one of the monomers in block A might be substituted with a side chain group as previously described.

In another aspect, the invention relates to a drug composition made up of a block copolymer at least one of formulas (I)–(X), wherein the A-type and B-type blocks are substantially made up of repeating units of formula —O—$R^5$, where $R^5$ is:

(1) —$(CH_2)_n$—$CH(R^6)$—, wherein n is zero or an integer from about 1 to about 5 and $R^6$ is hydrogen, cycloalkyl having about 3 to about 8 carbon atoms, alkyl having about 1 to about 6 carbon atoms, phenyl, alkylphenyl wherein the alkyl has about 1 to about 6 carbon atoms, hydroxy, hydroxyalkyl, wherein the alkyl has about 1 to about 6 carbon atoms, alkoxy having about 1 to about 6 carbon atoms, an alkyl carbonyl having about 2 to about 7 carbon atoms, alkoxycarbonyl, wherein the alkoxy has about 1 to about 6 carbon atoms, alkoxycarbonylalkyl, wherein the alkoxy and alkyl each independently has about 1 to about 6 carbon atoms, alkylcarboxyalkyl, wherein each alkyl independently has about 1 to about 6 carbon atoms, aminoalkyl wherein the alkyl has about 1 to about 6 carbon atoms, alkylamine or dialkylamino, wherein each alkyl independently has about 1 to about 6 carbon atoms, mono- or di-alkylaminoalkyl wherein each alkyl independently has about 1 to about 6 carbon atoms, chloro, chloroalkyl wherein the alkyl has from about 1 to about 6 carbon atoms, fluoro, fluoroalkyl wherein the alkyl has from about 1 to about 6 carbon atoms, cyano or cyano alkyl wherein the alkyl has from about 1 to about 6 carbon atoms or carboxyl;

(2) a carbocyclic group having about 3 to about 8 ring carbon atoms, wherein the group can be for example, cycloalkyl or aromatic groups, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substitutions, or (3) a heterocyclic group, having about 3 to about 8 ring atoms, which can include heterocycloalkyl or heteroaromatic groups, which can include from about 1 to about 4 heteroatoms selected from the group consisting of oxygen, nitrogen, sulfur and mixtures thereto, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substitutions.

Preferably, n is an integer from about 1 to about 3. The carbocyclic or heterocyclic groups comprising R 5 preferably have from about 4 to about 7 ring atoms, more preferably about 5 about 6. Heterocycles preferably include from about 1 to about 2 heteroatoms, more preferably, the heterocycles have one heteroatom. Preferably, the heterocycle is a carbohydrate or carbohydrate analog.

Those of ordinary skill will recognize that the monomers required to make these polymers are synthetically available. See, Vaughn et al., *J. Am. oil Chem. Soc.* 28: 294 (1951). In some cases, polymerization of the monomers will require the use of suitable protective groups, as will be recognized by those of ordinary skill in the art. Generally, the A and B-type blocks are at least about 80% comprised of —$OR^5$— repeating units, more preferably at least about 90%, yet more preferably at least about 95%.

In another aspect, the invention relates to a drug composition made up of a block copolymer of one of formulas (I)–(X) wherein the A-type and B-type blocks consist essentially of repeating units of formula —O—$R^7$, wherein $R^7$ is a $C_1$ to $C_6$ alkylene group.

The Hansch-Leo estimate of the octanol-water partitioning coefficient (P) for an organic molecule is calculated by the following formula:

$$\text{Log } P = a_n f_n + \Sigma b_m F_m$$

where the $f_n$ values are the fragmental constants for the different groups in the molecule, the an values are the number of any type of group in the molecule, the FM values are factors for certain molecular features such as single bonds or double bonds, and the bm values are the number of any such molecular feature. For instance, the Hansch-Leo fragmental constant for an ethylene oxide repeating unit (—$CH_2CHO$—) would be:

$$2f_c + 4f_H + f_0 + (4-1)F_b = 2(0.20) + 4(0.23) + (-1.82) + 3(-0.12) = -0.86$$

The Hansch-Leo fragmental constant for a propylene oxide (—$CH_2CH(CH_3)O$—) repeating unit would be:

$$2f_c + f_{CH3} + 3fH + f_0 + (4-1)F_b = 2(0.2) + 0.89 + 3(0.23) + (-1.82) + 3(-0.12) = -0.2$$

Those of ordinary skill in the art will recognize that the Hansch-Leo approach to estimating partition constants, in which approach the Hansch-Leo fragmental constants are applied, does not yield precisely the empirical partition constant. See Hansch and Leo, *Substituent Constants for Correlation Analysis in Chemistry and Biology*, Wiley, New York, 1979; James, *Solubility and Related Properties*, Marcel Dekker, New York, 1986, pp. 320–325. However, the approach is precise enough to define the hydrophobicity features of the polymeric delivery vehicle.

The block copolymers utilized in the invention will preferably form micelles in isotonic aqueous solutions at a physiological temperature having diameter from about 10 nm to about 100 nm. Micelles are supramolecular complexes of certain amphiphilic molecules that form in aqueous solutions due to microphase separation of the nonpolar portions of the amphiphiles. Micelles form when the concentration of the amphiphile reaches, for a given temperature, a CMC that is characteristic of the amphiphile. By varying the sizes of the hydrophilic and hydrophobic segments of the block copolymers, the tendency of the copolymers to form micelles at physiological conditions, as well as the average size of the micelles formed at physiological conditions, can be varied. These tendencies can also be adjusted by blending copolymers with differing mixes of hydrophobic and hydrophilic blocks. The micelles have a dense core formed by the water insoluble repeating units of the B blocks and lipophilic portions of a biological agent dissolved therein, and a hydrophilic shell formed by the A blocks and hydrophobic portions of the biological agent. The micelles have translational and rotational freedom in aqueous environment, and aqueous environments containing the rnicelles have low viscosity similar to water. Micelle formation typically occurs at copolymer concentrations from about 0.001 to 5% (w/v)

The small size of the micelles formed by block copolymers of the invention is believed to allow these micelles to penetrate in small capillaries and to be taken up by cells. The micelles also can incorporate large amounts of appropriate biological agents. For instance, micelles formed by Pluronic L61 can incorporate at least 1 mg of doxorubicin per 2 mg of copolymer.

The effective retention of a drug within the micelles of the invention can be quantified in terms of the partitioning coefficient (P) determined using formula:

$$P=[Agent]_m/[Agent]aq$$

where $[Agent]_{aq}$ is the concentration of biological agent in an aqueous environment outside of the micelles and $[Agent]_m$ is the concentration of agent in the micelles. In some cases, P is easily and accurately estimated based on the difference fluorescence properties of certain agents when in an aqueous vs. a more hydrophobic environment.

A minor portion of a targeting molecule made up of a targeting moiety coupled to a lipophilic moiety comprising a hydrocarbon having from about 3 to about 41 carbon atoms is incorporated into the micelles of the compositions of the targeting embodiment of the invention. This portion typically comprises no more than about 10% w/w of the copolymer components of a composition. The lipophilic moieties are believed to act as hydrophobic "anchors", which are incorporated non-covalently into the block-copolymer micelles so that the targeting moiety becomes part of, but extends beyond, the micelle. Such targeting moieties are preferably also incorporated into the micelles used in the brain chemotherapy embodiment of the invention. However, for the brain chemotherapy embodiment the lipophilic moiety can be any lipophilic moiety effective to non-covalently associate the targeting moiety with the micelles. For the brain chemotherapy embodiment, the lipophilic moiety can be, for example a fatty acid residue, a lipid, phospholipid, or a natural or synthetic polymer. Because of availability and ease of use, lipophilic moieties containing hydrocarbon groups such as fatty acid residues are preferred.

The targeting moieties have affinity for a cellular, tissue, viral or substratum site. Typical targeting moieties include without limitation antibodies and hormones with affinity for a cellular binding component, any molecule containing a carbohydrate moiety recognized by a cellular binding component and drugs that bind to a cellular binding component. The phrase "binding component" includes both receptor and acceptor molecules. Preferably, the binding component is a cell-surface binding component. Both polyclonal and monoclonal antibodies which are either available commercially or described in the literature can be employed. Alternatively the ligand can be a naturally occurring protein, such as insulin, that binds to a target site. A non-limiting example of a targeting moiety is the anti-$\alpha_2$-GP antibody to brain glial cells ($\alpha_2$-glycoprotein) which is described by Slepnev et al., *Bioconjugate Chem.* 3: 273–274 (1992).

To retain as much of the specificity of the polypeptide, preferably only one or two lipophilic moieties are bound to each polypeptide molecule. This binding can be achieved by the method described by Kabanov et al., *Protein Engineering*, 3, 39–42 (1989), the contents of which are incorporated herein by reference. In this method the lipophilic moiety or a reactive analog thereof is reacted with the targeting moiety in the presence of the surfactant sodium bis(2-ethylhexyl)sulfosuccinate {AOT®}, octane and a small amount of water will form reversed micelles, that is micelles with water on the inside and octane on the outside. These reversed micelles serve as microreactors allowing uniform point modification of the polypeptide molecules with lipophilic moieties. Reactive derivatives of fatty acids such as stearoyl chloride or lauroyl chloride can be reacted with polypeptides or other hydrophilic targeting moieties using this reaction system. Because the reaction system allows for the level of fatty acyl substitution to be limited, greater biological activity and solubility of the targeting moiety is generally preserved.

Routes of Administration

Oral delivery is the preferred method of administration for the instant compositions. For oral administration, the compositions can be used in the form of tablets capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the compositions can be combined with emulsifying and suspending agents. If desired, certain sweetening and/or flavoring agents can be added.

The pharmaceutical compositions of the invention can also be administered by a number of other routes, including without limitation, topically, rectally, vaginally, by pulmonary route, for instance, by use of an aerosol, or parenterally, including but not limited to intramuscularly, subcutaneously, intraperitoneally, intra-arterially or intravenously. The compositions can be administered alone, or can be combined with a pharmaceutically-acceptable carrier or excipient according to standard pharmaceutical practice.

For parenteral administration, sterile solutions of the conjugate are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

Suppository forms of the compositions of the invention are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycol of various molecular weights and fatty acid esters of polyethylene glycol. See Remington's Pharmaceutical Sciences, 16th Ed., Mack Publishing, Easton, Pa., 1980, pp. 1530–1533 for further discussion of suppository dosage forms. Analogous gels or creams can be used for vaginal, urethral and rectal administrations.

A variety of biological agents are suitable for use in the invention. These include, without limitation, proteins, peptides (e.g., oligopeptides and polypeptides) including cytokines, hormones (such as insulin), and the like, recombinant soluble receptors, monoclonal antibodies, human growth hormones, tissue plasminogen activators, clotting factors, vaccines, colony stimulating factors, erythropoietins, enzymes, and dismultase.

Preferred classes of biological agents (including chemotherapeutic agents) include anti-neoplastic agents, antibacterial agents, antiparasitic agents, anti-fungal agents, CNS agents, immunomodulators and cytokines, toxins and neuropeptides. Biological agents for which target cells tend to develop resistance mechanisms are also preferred. Particularly preferred biological agents include anthracyclines such as doxorubicin, daunorubicin, epirubicin, idarubicin, mithoxanthrone or carminomycin, vinca alkaloids, mitomycin-type antibiotics, bleomycin-type antibiotics, azole antifungals such as fluconazole, polyene antifungals such as amphotericin B, taxane-related antineoplastic agents such as paclitaxel and immunomodulators such as tumor necrosis factor alpha (TNF-α), interferons and cytokines.

Preferred biological agents (including chemotherapeutic agents) include without limitation additional antifungal agents such as amphotericin-B, flucytosine, ketoconazole, miconazole, itraconazole, griseofulvin, clotrimazole, econazole, terconazole, butoconazole, ciclopirox olamine, haloprogin, toinaftate, naftifine, nystatin, natamycin, undecylenic acid, benzoic acid, salicylic acid, propionic acid and caprylic acid. Such agents further include without limitation antiviral agents such as zidovudine, acyclovir, ganciclovir, vidarabine, idoxuridine, trifluridine, foxcarnet, amantadine, rimantadine and ribavirin. Such agents further include without limitation antibacterial agents such as penicillin-related compounds including 9-lactam antibiotics, broad spectrum penicillins and penicillinase-resistant penicillins (such as methicillin, nafcillin, oxacillin, cloxacillin, dicloxacillin, amoxicillin, ampicillin, ampicillin-sulbactam, azocillin, bacampicillin, carbenicillin, carbenicillin indanyl, cyclacillin, mezlocillin, penicillin G, penicillin V, piperacillin, ticarcillin, imipenem and aztreonam), cephalosporins (cephalosporins include first generation cephalosporins such as cephapirin, cefazolin, cephalexin, cephradine and cefadroxil; second generation cephalosporins such as cefamandole, cefoxitin, cefaclor, cefuroxime, cefuroxime axetil, cefonicid, cefotetan and ceforanide; third generation cephalosporins such as cefotaxime, ceftizoxime, ceftriaxone, cefoperazone and ceftazidime), tetracyclines (such as demeclocytetracycline, doxycycline, methacycline, minocycline and oxytetracycline), beta-lactamase inhibitors (such as clavulanic acid), aminoglycosides (such as amikacin, gentamicin C, kanamycin A, neomycin B, netilmicin, streptomycin and tobramycin), chloramphenicol, erythromycin, clindamycin, spectinomycin, vancomycin, bacitracin, isoniazid, rifampin, ethambutol, aminosalicylic acid, pyrazinamide, ethionamide, cycloserine, dapsone, sulfoxone sodium, clofazimine, sulfonamides (such as sulfanilamide, sulfamethoxazole, sulfacetamide, sulfadiazine, and sulfisoxazole), trimethoprim-sulfamethoxazole, quinolones (such as nalidixic acid, cinoxacin, norfloxacin and ciprofloxacin), methenamine, nitrofurantoin and phenazopyridine. Such agents further include agents active against protozoal infections such as chloroquine, diloxanide furoate, emetine or dehydroemetine, 8-hydroxyquinolines, metronidazole, quinacrine, melarsoprol, nifurtimox, pentamidine, sodium stibogluconate and suramin.

A variety of central nervous system agents are suitable for use in the present composition. These include neuroleptics such as the phenothiazines (such as compazine, thorazine, promazine, chlorpromazine, acepromazine, aminopromazine, perazine, prochlorperazine, trifluoperazine, and thioproperazine), rauwolfia alkaloids (such as reserpine and deserpine), thioxanthenes (such as chlorprothixene and tiotixene), butyrophenones (such as haloperidol, moperone, trifluoperidol, timiperone, and droperidol), diphenylbutylpiperidines (such as pimozide), and benzamides (such as sulpiride and tiapride); tranquilizers such as glycerol derivatives(such as mephenesin and methocarbamol), propanediols (such as meprobamate), diphenylmethane derivatives (such as orphenadrine, benzotrapine, and hydroxyzine), and benzodiazepines(such as chlordiazepoxide and diazpam); hypnotics (such as zolpdem and butoctamide); 9-blockers (such as propranolol, acebutonol, metoprolol, and pindolol); antidepressants such as dibenzazepines (such as imipramine), dibenzocycloheptenes (such as amitriptyline), and the tetracyclics (such as mianserine); MAO inhibitors (such as phenelzine, iproniazide,and selegeline); psychostimulants such as phenylethylamine derivatives (such as amphetamines, dexamphetamines, fenproporex, phentermine, amfepramone, and pemline) and dimethylaminoethanols (such as clofenciclan, cyprodenate, aminorex, and mazindol); GABA-mimetics (such as progabide), alkaloids (such as co-dergocrine, dihydroergocristine, and vincamine); cholinergics (such as citicoline and physosigmine); vasodilators (such as pentoxifyline); and cerebro active agents (such as pyritinol and meclofenoxate); as well as mixtures of several such agents.

Of particular interest are sedative-hypnotics such as the benzodiazepines, psycho-pharmacological agents such as the phenothiazines, thioxanthenes, butyrophenones, and dibenzoxazepines, and central nervous system stimulants. Since, the brain treatment embodiment of the invention is directed to compositions that improve the activity of biological agents, this embodiment of the invention can be applied to a wide variety of central nervous system agents by applying the principles and procedures described herein.

The compositions also can utilize a variety of polypeptides such as antibodies, toxins such as diphtheria toxin, peptide hormones, such as colony stimulating factor, and tumor necrosis factors, neuropeptides, growth hormone, erythropoietin, and thyroid hormone, lipoproteins such as α-lipoprotein, proteoglycans such as hyaluronic acid, glycoproteins such as gonadotropin hormone, immunomodulators or cytokines such as the interferons or interleukins, hormone receptors such as the estrogen receptor.

Preferred peptides are those with molecular weight of at least about 1,000, more preferably at least about 5,000, most preferrably at least about 10,000.

The block copolymers also can be used with enzyme inhibiting agents such as reverse transcriptase inhibitors, protease inhibitors, angiotensin converting enzymes, 5α-reductase, and the like. Typical of these agents are peptide and nonpeptide structures such as finasteride, quinapril, ramipril, lisinopril, saquinavir, ritonavir, indinavir, nelfinavir, zidovudine, zalcitabine, allophenylnorstatine, kynostatin, delaviridine, bis-tetrahydrofuran ligands (see, for example Ghosh et al., *J. Med. Chem.* 39(17): 3278–90 1966), and didanosine. Such agents can be administered alone or in combination therapy; e.g., a combination therapy utilizing saquinavir, zalcitabine, and didanosine or saquinavir, zalcitabine, and zidovudine. See, for example, Collier et al., *Antiviral Res.*, 1996 Jam. 29(1): 99.

Where cytokines are to be used, the cytokine of choice (which may include a mixture of several cytokines) is preferably either covalently modified with a hydrophobic substituent (e.g., a fatty acid or lipid residue), or incorporated into a micelle of a block copolymer of poly(oxyethylene)-poly(oxypropylene) (POE-POP) in an aqueous dispersion, or covalently modified with a hydrophobic substituent, and then incorporated into a micelle of a block-copolymer of poly(oxyethylene)-poly(oxypropylene) as described herein.

Incorporation of a cytokine into block copolymer micelles is performed either noncovalently by solubilization of cytokine in block copolymer aqueous solution, or covalently by cytokine conjugation with the block-copolymer and subsequent solubilization of the obtained conjugate in the block copolymer aqueous solution.

Both a cytokine covalent modification with a hydrophobic substituent and incorporation of a cytokine (either unmodified or modified with a hydrophobic group into a block copolymer micelle) lead to enhancement of specific immunomodulatory activity of this cytokine, and reduction of its side effects on the patient. These effects result from: {i} the increase of apparent affinity of a modified or micelle-incorporated cytokine to receptor-bearing (target) cells, {ii} increase of the efficacy of the cytokine penetration into the target cells, and {iii} decrease of cytokine nonspecific interactions with organs and tissues other than those providing its immunomodulatory effect.

A variety of human and animal cytokines are suitable for use in the present compositions. These include interferons, interleukins, tumor necrosis factors (TNFs) such as TNFα, and a number of other protein and peptide factors controlling functions of the immune system. It will be appreciated that this extends to mixtures of several such agents, and the invention is not directed to the underlying specific activity of the cytokines themselves, but rather to the compositions themselves.

Cytokine covalent modification with a hydrophobic substituent can be performed in reversed micelles of AOT® in octane that serve as microreactors allowing uniform point modification of peptide or protein molecules with fatty acid or lipid residues (1 to 5 residues per protein or peptide molecule). This makes it possible to preserve the water solubility and biological activity of modified agents. Kabanov, etal., *Protein Engineering*, 3(1), 39–42 (1989).

Additional chemotherapeutic agents appropriate for use in this invention include, without limitation, vinca alkaloids such as vincristine and vinblastine, mitomycin-type antibiotics such as mitomycin C and N-methyl mitomycin C, bleomycin-type antibiotics such as bleomycin A2, antifolates such as methotrexate, aminopterin, and dideazatetrahydrofolic acid, colchicine, demecoline, etoposide, taxanes such as paclitaxel (Taxol®), anthracycline antibiotics and others. The anthracycline antibiotics exemplify drugs having delivery problems due to low stability, the development of drug resistance in the target tissue, or rapid metabolism. These antibiotics typically include a fused tetracycline aglycone ring system joined at the 7-position to daunosamine. They include, for instance, the compounds represented by the formula:

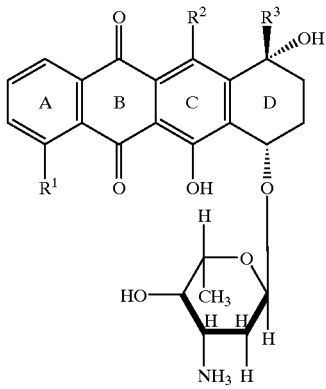

wherein $R^1$ is hydroxy or methoxy; $R^2$ is hydrogen or hydroxy; and $R^3$ is ethyl, acetyl, hydroxyacetyl, or an ester of hydroxyacetyl. These tetracycline antibiotics, like many anti-neoplastic agents, are believed to act by intercalating between the planar aromatic ring structures of DNA, thereby interfering with DNA replication. See, Neidle and Waring, *Molecular Aspects of Anti-Cancer Drug Action*, Pitman Press (1983). Neoplastic cells are generally particularly susceptible, since they are actively replicating and thus synthesizing replica copies of their DNA. Such tetracycline antibiotics include, without limitation, doxorubicin, daunorubicin, carminomycin, epirubicin, idarubicin, mithoxanthrone, 4-demethoxy-daunomycin, 11-deoxydaunorubicin, 13-deoxydaunorubicin, adriamycin-14-benzoate, adriamycin-14-octanoate, or adriamycin-14-naphthaleneacetate.

Dosage

The dosage for a biological agent in a micellar composition will often be about that of the biological agent alone; dosages will be set by the prescribing medical professional considering many factors including the age, weight and condition of the patient and the pharmacokinetics of the agent. Often the amount of a micellar form of an agent required for effective treatment may be less than the amount required using the free biological agent. By way of example, for daunorubicin use in treating cancer, a typical dosage will be about 1.0 mg per kg of body weight. Vinblastine is typically administered at a dose of from 0.1 to 0.2 mg per kg of body weight.

Generally, the biological agents used in the invention are administered to an animal in an effective amount. The effect of the copolymer used in the composition on effectiveness must be considered in determining effective amount. Generally, an effective amount is an amount effective to either (1) reduce the symptoms of the disease sought to be treated or (2) induce a pharmacological change relevant to treating the disease sought to be treated. For cancer, an effective amount includes an amount effective to: reduce the size of a tumor; slow the growth of a tumor; prevent or inhibit metastases; or increase the life expectancy of the affected animal.

In many cases, the metabolites of various biological agents create or enhance the unwanted effects resulting from administering the agent. This is certainly the case for anthracycline-based drugs, where metabolites are believed to lead to cardiotoxicity. See, Mushlin et al., *Br. J. Pharmacol.* 110: 975–982 (1993). The copolymer compositions of the invention can decrease the rate of metabolism for biological agents, thereby reducing the potential for harmful side effects.

Penetration of the brain by a biological agent can be measured by a number of techniques, as will be recognized by those of ordinary skill in the art. Such methods include isotope labeling, assessing animal behavior for the effects of a biological agent, and measuring lethal dosages for drugs with toxic effects that occur at the brain. Such methods further include measuring decreases in the dosage required to elicit the appropriate biological response.

Various antifungal agents successfully treat human fungal infections. However, the therapeutic dose is often a compromise between achieving effective drug levels and avoiding toxic side effects. In recent years, the emergence of drug resistance among intrinsically sensitive species such as *Candida albicans* and the increasing incidence of intrinsically drug resistant species such as *Candida kruset* has prompted a search for newer antifungal agents.

Although fluconazole has a low incidence of side effects, the incidence of resistance is an increasing problem. Delivery vehicles that are effective in enhancing chemotherapeutic activity and reversing resistance to such agents is therefore desirable for this agent, as well as for other antimicrobial agents.

The following examples will serve to further typify the nature of the invention but should not be construed as a limitation on the scope thereof, which is defined solely by the appended claims.

EXAMPLE 1

Micelle Size

Block copolymers of poly(oxyethylene)-poly (oxypropylene) having the ratios of poly(oxypropylene) to poly(oxyethylene) indicated below were dispersed in RPMI 1640 medium at the concentrations indicated below. The mixtures were incubated for 40 minutes at 300C. The average micelle diameter was measured by quasielastic light scattering. See Kabanov et al., *Macromolecules* 28: 23032314, 1995. The results were as follows:

| Copolymer | Conc. (% w/v) | Avg. Diameter |
|---|---|---|
| F-68 | 1.0% | 726.0 nm |
| P-85 | 1.0% | 18.0 nm |
| L-64 | 1.0% | 20.4 nm |
| 1:1.5 P-85:L-64 | 0.01% | 17.0 nm |
| 1:2.5 F-68:L-64 | 1.0% | 33.5 nm |

EXAMPLE 2

Fatty Acyl Conjugates

A solution of 50 $\mu$l of 2 mg/ml of anti-$\alpha_2$ GP antibody specific for the $\alpha_2$-glycoprotein of glial cells (Chekhonin et al., *FEBS Lett*. 287: 149–152, 1991) in 0.1 M borate buffer (pH 8.5) was mixed into 2 ml of 0.1M AOT® sodium bis(2-ethylhexyl)sulfosuccinate, available from Serva Chemicals, Germanyl in octane. A reaction is initiated by adding a two-fold molar excess (with respect to the polypeptide) of stearic acid chloride in 0.2 ml of 0.1M AOT® in octane to the mixture. The stearic acid chloride was obtained from stearic acid (available from Reakhim, Russia) as described in Kabanov et al., *Molek Biologiya (Russian)*, 22: 473–484 (Engl. edn.: 382–391), 1988. The reaction was conducted overnight at 25° C. The product is precipitated three times with cold acetone, dissolved in RPMI 1640 medium and sterilely filtered through a 0.22 $\mu$m filter (the polygonal antibody used in this experiment also reacted with glial fibrillary acidic protein.).

EXAMPLE 3

Iodinated Targeting Moieties

Anti-$\alpha_2$ GP antibody was labeled with $^{125}$I using Bolton-Hunter reagent in the system of reversed micelles of AOT® in octane as described in Slepnev V. I. et al, *Bioconjugate Chem*., 3, 273–274 (1992). Specific radioactivity of the $^{125}$I-labeled protein ranges from 19 to 21 Ci/mol.

Wistar rats (80 g body weight, 8 animals/group) were injected i.p. (0.1 mi/10g body weight) with a composition made up of the $^{125}$I-labeled anti-$\alpha_2$-GP antibody (1 mCi/ml) dissolved in a mixture of 1.5% (w/v) copolymer Pluronic P85 and 2.5% (w/v) copolymer Pluronic L64 dissolved in RPMI 1640 medium. $^{125}$I-labeled polypeptide dissolved in RPMI 1640 medium was administered at the same concentration. After three days the animals were killed, and tissue samples taken for radioactivity assay to analyze tissue distribution as described by Chekhonin et al., *FEBS Lett*., 287, 149–152 (1991). The distribution of radioactivity was quantitated by liquid scintillation counting. The experiments were repeated at least twice and the results were reproducible with less than 10% variation. The results, expressed as the ratio of brain radioactivity to the radioactivity in a given tissue (±S.D.), were as follows.

| | Relative Content of Label | |
|---|---|---|
| Organ | Micelle | Control |
| Brain/heart | 1.22 ± 0.91 | 0.11 ± 0.02 |
| Brain/kidney | 7.42 ± 0.56 | 0.05 ± 0.01 |
| Brain/liver | 9.02 ± 0.75 | 0.01 ± 0.00 |
| Brain/lung | 12.1 ± 0.92 | 0.04 ± 0.01 |
| Brain/spleen | 6.48 ± 0.39 | 0.01 ± 0.00 |
| Brain/blood | 8.85 ± 0.67 | 0.01 ± 0.00 |

EXAMPLE 4

Quantitation of Behavioral Changes

Quantitative evaluation of changes in behavior reactions {See *Theory in Psychopharmacology*, S. J. Cooper, Ed., Vol. 1, (Academic Press, London, New York, 1981) are performed. Groups (10 animals/dose point) of DBA/2 male mice (from Kriukovo Veterinary Department of Russian Academy of Sciences, Russia, 20–25 g body weight) with similar characteristics of moving activity are injected i.p. with the test preparations at doses corresponding to 0.10 $LD_{95}$, Concentrations are adjusted so that a maximum volume of 0.1 ml is injected in each mouse. Mouse mobility (the number of mouse migrations in a cell) and grooming characteristics are registered for each group at 30 minute intervals over 15 hours using a Rhema Labortechnik device. The experiments are repeated three times.

EXAMPLE 5

Measuring Toxicity

The lethal effect accompanied by development of specific neurologic symptoms described in *Theory in Psychopharmacology*, S. J. Cooper, Ed., Vol. 1, (Academic Press, London, New York, 1981) is measured. Groups (10 animals/dose point) of DBA/2 mice (18–19 g body weight)

are injected i.p. with the test preparations. Concentrations are adjusted so that a maximum volume of 0.5 mL is administered to each mouse. For quantitative evaluation of specific lethal action, the lethal dose (L.D.) is calculated using the probit method on the basis of 10 concentration points. The experiments are repeated at least twice and results should reproducible with less than 10% variation.

EXAMPLE 6A

Micelle Formation

A 1:1.5 mixture of Pluronic P85 and Pluronic L64 having individual ratios (n) of (oxypropylene) to (oxyethylene) blocks of 1.00 and 1.50, respectively, and a combined value (N) of 1.30, was diluted with RPMI 1640 medium to a final concentration of 4.0% at 40° C. The mixture was incubated for 30 minutes at 37° C. and then sterilized by filtration through a 0.22 μm filter. An equal volume of a solution of 200 μg daunorubicin in RPMI 1640 medium was added and this mixture was incubated for 30 minutes at 37° C.

EXAMPLE 6B

Preparation of Brain Targeted Micelles

Equal volumes of the solution of Pluronic micelles of Example 6A and the solution of stearylated antibody of Example 2 were mixed at 37° C. Equal volumes of the resulting solution and a sterile 6 μg/ml solution of haloperidol dissolved in RPMI 1640 were mixed at 37° C.

EXAMPLE 7

Behavioral Measure of Brain Biodistribution

The preparations described in Example 6, except that the anti-GFAP antibody was not radioactive and was used at a concentration of 0.4 mg/ml, were used in these experiments.

Solutions were administered i.p. Animal mortality was monitored daily for 14 days. The $LD_{50}$ and maximum tolerated dosage ("M.T.D.", i.e., the maximal dose at which no animals among 6 equivalently treated animals died) were calculated by probit analysis. See, Chan and Hayes in *Principles and Methods of Toxicology*, Hayes, A. W., Raven Press, New York, 1989, pp. 169–189. When administered in the Pluronic vehicle, the $LD_{95}$ value of haloperidol was determined to be 0.15 mg/kg, without the Pluronic vehicle, the $LD9_5$ value of haloperidol was 75 mg/kg.

An amount equaling 10% of the $LD_{95}$ for a given composition was injected i.p. into DBA/2 mice in 0.5 ml of the pluronic vehicle (Example 6). The behavioral results of these injections (±S.D.), measured as described in Kabanov et al., *J. Controlled Release*, 22:141 (1992), were as follows:

| Behavior | Micellar form of haloperidol | Free haloperidol |
| --- | --- | --- |
| Horizontal mobility | 14.4 ± 64% | 204.6 ± 24% |
| Grooming | 26.5 ± 76% | 1834.8 ± 12.5% |

As can be seen from the above table, the micellar form of haloperidol is markedly more active than an amount of free haloperidol normalized at 10% of the $LD_{95}$ amount.

EXAMPLE 8

Specific and Non-Specific Targeting Molecules

A specific targeting composition was prepared as described in Example 6. The final concentration of the anti-GFAP antibody was 0.02 mg/ml, and its specific radioactivity was 20 Ci/mol.

A non-specific was prepared using the same procedure but substituting a Fab preparation of non-specific murine IgG for the brain-specific antibody. The final concentration of the antibody was 0.02 mg/ml, and its specific radioactivity was 20 Ci/mol.

These preparations (0.5 ml) were injected i.p. into DBA/2 mice. The resulting biodistributions (±S.D.) were

| Organ | Relative Content of label (% Dose/g of tissue) | |
| --- | --- | --- |
| | Micelle | Control |
| Brain | 53 + 4.15* | 1.4 + 0.12 |
| Heart | 3.2 + 0.22 | 3.1 + 0.21 |
| Kidney | 4.4 + 0.31 | 5.1 + 0.47 |
| Liver | 4.3 + 0.26 | 36.2 + 1.92 |
| Lung | 2.2 + 0.11 | 4.8 + 0.42 |
| Spleen | 4.1 + 0.33 | 5.1 + 0.41 |
| Blood | 3.8 + 0.31 | 8.7 + 0.67 |

EXAMPLE 9

Targeting Using Neuronal-Specific Anti-Enolase Antibody

A targeting composition was made using the procedure of Example 6 wherein the antibody was a monoclonal antibody against the y-subunit of neuronal-specific enolase ("anti-NSE MAb", available from Russian Research Center, Moscow, Russia). The final concentration of the antibody was 0.35 mg/ml, and its specific radioactivity was 18 Ci/mol. For control experiments, the nonspecific murine antibody preparation described in Example 8 was used.

These preparations (0.5 ml) were injected i.p. into DBA/2 mice. The resulting biodistributions (±S.D.) were:

| Organ | Relative Content of label (% Dose/g of tissue) | |
| --- | --- | --- |
| | Micelle | Control |
| Brain | 58 + 5.12* | 0.9 + 0.06 |
| Heart | 3.2 ± 0.23 | 2.8 ± 0.21 |
| Kidney | 4.3 ± 0.36 | 5.6 ± 0.52 |
| Liver | 3.8 ± 0.32 | 31.2 ± 3.05 |
| Lung | 2.10 ± .18 | 6.4 ± 0.59 |
| Spleen | 3.9 ± 0.33 | 4.9 ± 0.37 |
| Blood | 4.1 ± 0.40 | 7.4 ± 0.71 |

EXAMPLE 10

Targeting Using Insulin

An insulin targeting molecule was prepared by linking stearyl moieties to insulin (available from Sigma, St. Louis, Mo.) using the method of Example 6. The targeting molecule was incorporated into a haloperidol composition using the method described in Example 6. The final concentration of insulin in the composition was 0.4 mg/ml. The $LD_{95}$ for this haloperidol composition was determined to be 3.0 mg/kg, using the method in Example 7.

An amount equaling 10% of the $LD_{95}$ for a given composition was injected i.p. into DBA/2 mice in 0.5 ml (6 mice per each treatment). The behavioral results of these injections (±S.D.), measured as described in Kabanov et al., *J. Controlled Release*, 22:141(1992), were as follows:

| Behavior | Micellar form of haloperidol | Free haloperidol |
|---|---|---|
| Horizontal mobility | 56.1 ± 36% | 180.1 ± 26% |
| Grooming | 86.6 ± 29% | 1656.4 ± 6.5% |

As can be seen from the above table, the micellar form of haloperidol is markedly more active an amount of free haloperidol normalized at 10% of the $LD_{95}$ amount.

EXAMPLE 11

Sulpiride Compositions

Sulpiride and the stearylated anti-NSE Fab antibody preparation of Example 9 were orporated into the block-copolymer micelles using the methods described in Example 6. The al concentration of anti-NSE Fab in the preparation was 2.1 mg/ml. A sterile, control solution sulpiride in RPMI 1640 medium was prepared The $LD_{95}$ values for the preparations was termined as described in Example 7. For the block copolymer preparation, the $LD_{95}$ was 12.1 mg/kg body weight; for the control preparation it was 100 mg/kg body weight.

EXAMPLE 12

Trifluorperazine Compositions

Trifluorperazine and anti-GFAP Fab antibody preparation treated with stearoyl chloride were incorporated into the block-copolymer micelles using the methods described in Example 6. The final concentration of antibody in the preparation was 0.2 mg/ml. A sterile, control solution of trifluorperasin in RPMI 1640 medium was prepared. The $LD_{95}$, values for the preparations was determined as described in Example 7. For the block copolymer preparation, the $LD_{95}$ was 0.04 mg/kg body weight; for the control preparation it was 10 mg/kg body weight.

The minimum neuroleptic dose (MND) was determined for each preparation. The minimum neuroleptic dose is defined as the minimum dose that caused a neuroleptic effect as monitored behaviorally. See, Kabanov et al., *FEBS Lett.* 258: 343–345, 1989. The MND for the copolymer-containing preparation was 0.02 mg/kg, while that of the control preparation was 2 mg/kg. The ratio of $LD_{95}/MND$ was 50 for the copolymer preparation and 5 for the control preparation.

EXAMPLE 13A

Cytotoxicity Against Resistant Cancer Cells

Pluronic P85 was dissolved in RPMI 1640 medium (ICN Biomedicals Inc., Costa Mesa, Calif.) to a final concentration of 1.0%, and then the solution was sterilized by filtration to remove bacterial or fungal contamination. This Pluronic P85 solution was used to make appropriate dilutions of sterile drug solutions for the cell culture experiments described below.

The cytotoxicity studies utilized the SKOV3 line of transformed cells (hereinafter "SK cells") and the SKVLB cell line derived therefrom (hereinafter "SK-resistant cells"). Both of these cell lines were provided by Dr. V. Ling, University of Toronto. The SK-resistant cell line is a multidrug resistant cell line derived from the SK cell line by long term cultivation in the presence of vinblastine.

Various dilutions of a number of anticancer agents were made in RPMI medium or the Pluronic P85 solution described above. Cells were prepared for use in these experiments by plating an equal volume of a cell suspension (2000–3000 cells) into the wells of 96-well microliter plates (Costar, Cambridge, Mass.) and cultured for 2 days. All cell culturing was done at 37° C. and under a 5% $CO_2$ atmosphere. After this, 100 μl per plate of fresh medium (RPMI 1630 medium supplemented with 10% fetal calf serum) was added. The free anticancer agent or copolymer plus anticancer agent dilutions were applied to the wells in 100 μl volumes. The cells were exposed to the free or micellar form of a drug for two hours. After this incubation, the cells were washed three times with fresh medium. Then, the cells were cultured under fresh medium for an additional four days.

The number of viable cells for each culture was determined by standard XTT analysis, which measures the activity of mitochondrial enzymes. See, Scudiero et al., *Cancer Res.*, 48:4827 (1988). 50 μl per well of sterile 1 mg/ml XTT (2,3-bis[2Methoxy-4-nitro-5-sulfophenyl]-2H-tetrazolium-5carboxanilide inner salt, Sigma, St. Louis, Mo.) in PRMI-1640 containing 5 μl/ml of 1.54 mg/ml phenazine metasulphate (Sigma) in PBS was added to the cells. The cells were incubated for 16 hours, after which the absorbance of each well at 450 nm was determined. The SEM for any value determined (the mean of three determinations) was always with 10% of the value. $IC_{50}$ values (i.e., the concentration at which 50% inhibition was achieved) were determined by extrapolating from graphs plotting the number of viable cells (i.e., the mitochondrial enzyme activity) versus the concentration of drug applied to the cells. The results for SK-resistant cells were as follows:

| Form of biological agent | $10_{50}$, (ng/mi) |
|---|---|
| Free doxorubicin | 60,000 |
| Pluronic L61 | 70 |
| Pluronic P85 | 1000 |
| Pluronic F108 | 2000 |
| Pluronic F68 | 60,000 |

EXAMPLE 14

Copolymer Titrations

Figure 1B:
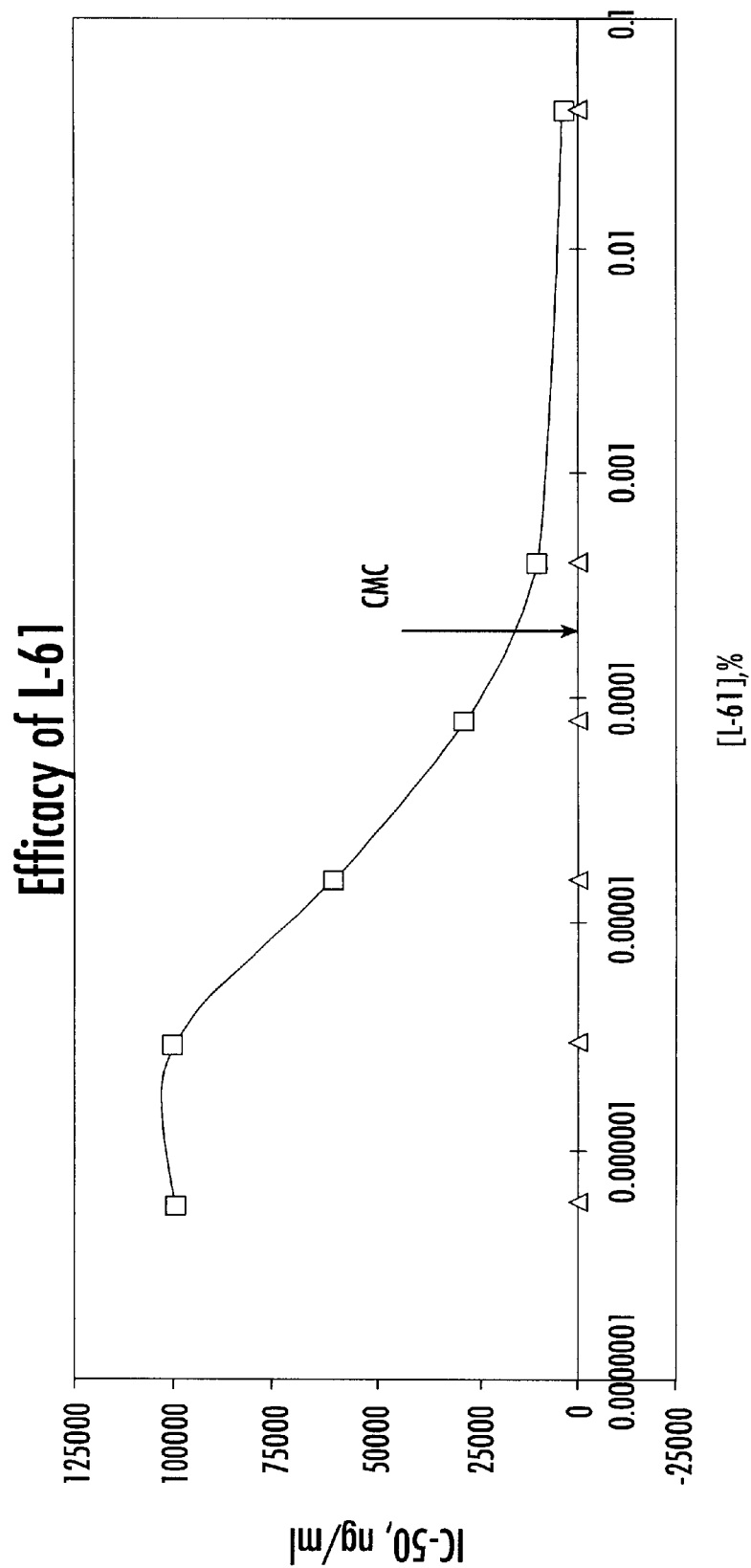

The methodology of Example 13A was used except in two details. The first difference was that doxorubicin-resistant MCF7 cells (MCF ADR cells, which described further in Example 21) were used in place of SK cells. Second, in addition to varying doxorubicin concentrations, the concentration of copolymer was also varied. The percent inhibition with change in doxorubicin concentration is shown in FIG. 1A for cultures maintained in the presence of varying concentrations of Pluronic L61. Line 1 is for free doxorubicin; line 2 is for doxorubicin in the presence of $0.61 \times 10^{-6}$M Pluronic L61; line 3 is for doxorubicin in the presence of $0.3 \times 10^{-5}$ M Pluronic L61; line 4 is for doxorubicin in the presence of $0.16 \times 10^{-4}$ M Pluronic L61; line 5 is for doxorubicin in the presence of $0.8 \times 10^{-4}$ M Pluronic L61; line 6 is for doxorubicin in the presence of $0.4 \times 10^{-3}$ M Pluronic L61; and line 7 is for doxorubicin in the presence of $0.4 \times 10^{-1}$ M Pluronic L61. In FIG. 1B, these data are consolidated such that the figure shows the $IC_{50}$ value for doxorubicin applied to the cells in the presence of the indicated concentration of Pluronic L61.

EXAMPLE 15

Parenteral Composition

A composition suitable for parenteral administration was prepared by dissolving 400 mg of Pluronic P-85 and 600 mg of Pluronic L-64 in 50 mL of RPMI 1640 at 40° C. The mixture was incubated for 30 minutes at 37° C. and then sterilized by filtration through a 0.22 gm filter. The filtered solution was mixed with a solution of 100 mg of sterile lyophilized haloperidol powder dissolved in 50 mL of RPMI and incubated for 30 minutes at 37° C.

The composition can be stored in the dark at room temperature for 7 days without loss of activity or can be lyophilized and stored for at least 1 year in the dark at room temperature.

EXAMPLE 16

Parenteral Composition

A further composition suitable for parenteral administration prepared by dissolving 100 mg of sodium ascorbate in 100 ml of a 9% aqueous solution of sodium chloride. To one-half of this solution were added at 4° C. 400 mg of Pluronic P-85 and 600 mg of Pluronic L-64. The mixture was incubated for 30 minutes at 37° C. and then sterilized by filtration through a 0.22 μm filter. Separately 100 mg of sterile lyophilized haloperidol powder and 50 mg of glucose were dissolved in the remaining sodium ascorbate-sodium chloride solution and the two solutions were mixed and incubated for 30 minutes at 37° C.

This composition can be stored for 30 days in the dark at room temperature without loss of activity or can be lyophilized and stored for at least 1 year in the dark at room temperature.

EXAMPLE 17

Parenteral Composition

A further composition suitable for parental administration prepared by dissolving 100 mg of sodium ascorbate in 100 mg of a 9% aqueous solution of sodium chloride. To one-half of this solution were added at 4° C. 400 mg of Pluronic P-85 and 600 mg of Pluronic L-64. The mixture was incubated for 30 minutes at 37° C. Separately 100 mg of lyophilized haloperidol powder and 50 mg of glucose were dissolved in the remaining sodium ascorbate-sodium chloride solution and the two solutions were mixed and incubated for 30 minutes at 37° C. The combined mixture was sterilized by filtration through a 0.22 μm filter. This composition can be stored for 30 days in the dark at room temperature without loss of activity or can be lyophilized and stored for at least 1 year in the dark at room temperature.

EXAMPLE 18

Parenteral Composition

A parenterally administrable composition was prepared by dissolving 400 mg of pluronic P-85 and 600 mg of pluronic L-64 in 50 ml of aqueous solution containing 1 mg/ml sodium ascorbate and 0.9 g/ml sodium chloride. The mixture was incubated for 30 min. at 37° C. To this was added 100 mg of lyophilized haloperidol powder and 50 mg of glucose dissolved in 50 ml of aqueous solution containing 1 mg/ml sodium ascorbate and 0.9 g/mi sodium chloride and this combined mixture was incubated for 30 min. at 37° C. To 100 ml of this preparation were dissolved 40 mg of fyophilized hydrophobized anti-GFAP Fab powder and this solution was incubated for 30 minutes at 37° C. and then sterilized by filtration through a 0.22 μm filter. The composition can be stored in the dark at room temperature for 30 days without any essential loss of activity or can be lyophilized and stored for at least one year in the dark at room temperature.

EXAMPLE 19

A further composition suitable for parenteral administration is prepared by dissolving 100 mg of sodium ascorbate in 100 ml of a 9% aqueous solution of sodium chloride. To this solution are added at 40° C. 10 mg of Pluronic L-61. The mixture is incubated for 30 minutes at 37° C. and then sterilized by filtration through a 0.22 μm filter. This solution is packaged together with a container of 10 mg doxorubicin.

EXAMPLE 20

Acute Toxicity

The acute toxicity of Pluronic F108, P85 and L61 were studies in 5-week old BALB/c male mice. Each experimental group of mice included 6 mice.

Various doses of isotonic Pluronic solutions were administered i.p. Animal mortality was monitored daily for 14 days. The $LD_{50}$ and maximum tolerated dosage ("MTD", i.e., the dose at which no animals among 6 equivalently treated animals died) were calculated by probit analysis. See, Chan and Hayes in *Principles and Methods of Toxicology*, Hayes, A. W., ed., Raven Press, New York, 1989, pp. 169–189. The results were as follows:

| Pluronic | MTD, g/kg | $LD_{50}$, g/kg |
|---|---|---|
| Pluronic L61 | 0.1 | 0.8 |
| Pluronic P85 | 0.2 | 0.8 |
| Pluronic F108 | 5.0 | 9.0 |

EXAMPLE 21

Antibodies (Ab) to GFAP and α2-glycoprotein were modified with stearic acid residues as described in Example 1. They were also covalently linked to Pluronic P85 as described by Kabanov et al., J. Controlled Release, 22:141 (1992).

The therapeutic efficacy of doxorubicin in treatment of glioma was explored. C6 glioma cells were inoculated intracerebrally in groups (n=25) of male Sprague-Dawley rats (280–300g) obtained from Kriukovo Department of Nursery of Russian Academy of Sciences. 10, 15, 20, and 25 days after inoculation, (a) 10 mg/kg of free doxorubicin, (b) doxorubicin in 1% Pluronic P85, (c) doxorubicin in 10% Pluronic P85 containing 0.1 mg/ml of Ab modified with stearic acid chloride and (d) doxorubicin in 10% Pluronic P85 containing 0.1 Mg/ml of Ab linked to Pluronic P85 were administered i.p. (volume 1 ml/300 g body weight). Controls will be given injections i.p. with an equal volume of saline. Clinical observations were performed daily. Animals were weighted weekly in the first 2 months and monthly thereafter. Vital signs will be verified to ensure that the animal was dead and necropsy was initiated within 5 min. after the animal died. Data on survival was analyzed to grade the drug effect on tumor incidence and latency. The data were presented as a ratio of median survival times in the treated group (T) and control (C). For necropsy all major organs were saved and fixed in their entirety. The tail (used in the study for animal identification during in-life phase) was saved in formalin with the animal tissues. All brains were removed and trimmed at three different positions. Three sections of the spinal cord were collected at the cervical, thoracic and lumbar level. Trimmed specimen was placed in Tissue Tek cassettes and processed in a tissue processor. Tissue sections were cut at a thickness of 4–6 mm using a microtome and stained with haematoxylin-eosine. Histopathological examinations of brains assessed: (i) the total number of tumors in animals; (ii) the number of tumor bearing animals; and (iii) the histopathological classification and grading of tumors. The results of the experiment are as follows:

| Animal group | Median survival, days | Trial/control × 100% |
|---|---|---|
| Control | 11.2 | — |
| Free doxorubicin | 10.5 | — |
| Micellar doxorubicin | 25.3 | 226 |
| Micellar doxorubicin + strearoylated antibodies | 41.0 | 366 |
| Aicellar doxorubicin + conjugated antibodies | 24.5 | 218 |

The histopathological examinations also revealed that (1) free doxorubicin caused no effect on tumor size and number compared to control; (2) all 3 micellar formulations caused significant decrease in tumor size and number (3) the most pronounced effect was observed in the case of micellar doxorubicin+strearoylated antibodies, in this case tumors were practically not observed.

EXAMPLE 22

In vivo Activity of Insulin Formulated During Oral Administration

Hypoglycemia induced by high doses of insulin in mice was used as biological response criteria. The drug activity was evaluated by analyzing the glucose level in plasma versus time following drug administration. Isotonic solutions of free insulin (Ins) or insulin formulated with POE-POP block copolymer ("SP1-Ins") were given to Balb/c mice at the same doses either s.c. or p.o.

Female six-week-old Balb/c mice (six animals per time point) were administered s.c. or p.o. with sterile 100 μl per 20 g of body weight (5 ml/kg) of Insulin or SP1-Insulin solutions, and the same volumes of isotonic solution were given to the control group of animals. Both Insulin and SP1-Insulin injections contained 0.02 mg/ml of insulin with activity of 27.3 μ/mg.

The animals were sacrificed after various time intervals (0.5–6hr; post-administration), plasma samples were collected, and glucose levels were analyzed by standard glucosoxidase-peroxidase method. The statistical significance was analyzed by the multiple range text of Duncan-Kramer.

Insulin, when injected s.c., induces a reversible decrease in the glucose level in plasma that reaches about 15% of the normal level 3 hours after drug administration, and then returns to the normal level after about 6 hours. The SP1-Insulin formulation given s.c. produced about the same changes as Insulin (data not shown). The comparison of p.o. administered formulations showed that SP1-Insulin, induces a significant decrease in the glucose level (about 28% of the normal level) with the same pattern of pharmacokinetics as s.c. administered drug, while Insulin given in the same way and at the same dose produces only minor changes.

The results of this study have shown that incorporation of insulin into the block copolymer carriers led to a substantial increase in its activity during oral administration, suggesting that bioavailability of orally administered SP1-Insulin is comparable to that of s.c. injected free insulin.

EXAMPLE 23

A. A block-copolymer of poly(oxyethylene)-poly (oxypropylene) in which N=1.00 (pluronic P785). is diluted with RPMI 1640 medium to a final concentration of 2.0% at 4° C. The mixture is incubated for 30 minutes at 37° C. and then sterilely filtered through a 0.22 μM filter. An equal volume of a sterile solution of human recombinant Interferon $\alpha_2$ in RPMI 1640 medium is added, and this mixture is incubated for 30 minutes at 37° C. (Prep. A).

B. Antiproliferative activity of Prep. A and nonmodified human recombinant Interferon $\alpha_2$ solution in RPMI 1640 medium (Prep. B) with respect to Jurkat cells was determined by flow cytometry by a decrease in the index of cell growth (ratio of the number of cells incubated with Prep. A or Prep. B for 24 hours to the initial number of cells). The results obtained are as follows:

| Concentration of Interferon | Index of cell growth ± S.D. | |
|---|---|---|
| $\alpha_2$, 1 g(M) | Prep. A | Prep. B |
| −16 | 1.68 ± 0.12 | 1.72 ± 0.11 |
| −15 | 1.24 ± 0.10 | 1.71 ± 0.15 |
| −14 | 1.20 ± 0.12 | 1.61 ± 0.17 |
| −13 | 1.14 ± 0.08 | 1.63 ± 0.13 |
| −12 | 1.21 ± 0.09 | 1.44 ± 0.12 |
| −11 | 1.16 ± 0.06 | 1.40 ± 0.11 |
| −10 | 1.20 ± 0.10 | 1.35 ± 0.12 |
| −9 | 1.11 ± 0.09 | 1.28 ± 0.08 |
| −8 | 1.18 ± 0.10 | 1.25 ± 0.10 |

EXAMPLE 24

A. Human recombinant Interferon-$\alpha_2$ was incorporated in block-copolymer of poly(oxyethylene)-poly(oxypropylene) micelles (N=1.0) as described in Example 23 (Prep. A). Nonmodified human recombinant Interferon-$\alpha_2$ solution in RPMI 1640 medium (Prep. B) was used as a control. Concentrations of Interferon-($\alpha_2$ in Prep. A and Prep. B were $1\times10^{-13}$M and $1\times10^{-10}$M respectively (according to the data represented in Example 23 these concentrations of Interferon-$\alpha_2$ in Prep. A and Prep. B produce same antiproliferative effect on Jurkat cells).

B. The antiproliferative activity of Prep. A and Prep. B was determined by flow cytometry analysis of the cell cycle distribution of Jurkat cells. The results obtained are as follows:

| Sample | G1/G0, % | S, % | G2 + M, % |
|---|---|---|---|
| Control (untreated cells) | 50.0 | 32.5 | 17.5 |
| Prep. B | 45.0 | 46.0 | 9.0 |
| Prep. A | 48.0 | 42.0 | 10.0 |

EXAMPLE 25

A. A 1:1.5 mixture of block copolymers of poly(oxyethylene)-poly(oxypropylene) (pluronics P-85 and L-64) having individual ratios (n) of (oxypropylene) to (oxyethylene) blocks of 1.00 and 1.50, respectively, and a combined value (N) of 1.30, is diluted with RPMI 1640 medium to a final concentration of 2.0% at 4° C. The mixture is incubated for 30 minutes at 37° C. and then sterilely filtered through a 0.22 μm filter (Prep. A).

B. 50 μl of 2 mg/ml. natural human Interferon-$\alpha_2$ in 0.1 M borate buffer (pH 8–5) were solubilized in 2 ml of 0.1 M AOT® in octane. A 100-fold molar excess (with respect to Interferon $\alpha_2$) of stearoyl chloride in 0.1 M AOT® in octane is added to the micellar system obtained. The reaction mixture is incubated overnight at 25° C. Stearoylated cytokine is precipitated three times with cold acetone, dissolved in RPMI 1640 medium and sterilely filtered through a 0.22 μm filter (Prep. B).

C. Modified human natural Interferon-$\alpha_2$ (Prep. B) was incorporated in block-copolymer of poly(oxyethylene)-poly(oxypropylene) in which N=1.30 (Prep. A) as described in Example 24 (Prep. C).

D. Antiviral activity of Prep. C and nonmodified native Interferon-$\alpha_2$ (Prep. D) used as a control was evaluated by suppression of the cytopathic action of vesicular stomatitis virus on 3T3 NIH cells. Prep. C and Prep. D were added to the cells 24 hours before their infection with a 100-fold lethal close of the virus. Antiviral effect was determined 24 hours after virus administration. Antiviral titer for Prep. C and Prep. D was determined to be $3 \times 10^9$ and $2 \times 10^5$ respectively.

EXAMPLE 26

A. Natural pork interferon-a. was modified with stearoyl chloride as described in Example 25 (Prep. A). Nonmodified native Interferon-α (Prep. B) used as a control.

B. Antiviral activity of Prep. A and Prep. B was evaluated by suppression of the cytopathic action of vesicular stomatitis virus on kidney cells of pork embryo. Prep. A and Prep. B were added to the cells 24 hours before their infection with a 100-fold lethal dose of the virus. Antiviral effect was determined 24 hours after virus administration. Antiviral titer for Prep. A and Prep. B determined to be $2 \times 10^8$ and $1 \times 10^4$ respectively.

EXAMPLE 27

A. Natural pork interferon-α was modified with phosphatidylinositol. To this end, 50 μl of 2 mg/ml interferon alpha in 0.1 M borate buffer (pH 8.5) are solubilized in 2 ml of 0.1M AOT® in octane. A 50-fold molar excess (with respect to Interferon-$\alpha_2$) of phosphatidylinositol, oxidized in advance by sodium periodate, in 0.1M AOT® in octane, and 100-fold molar excess of sodiumborhydride are added to the micellar system obtained. The reaction mixture was incubated overnight at 25° C. The modified cytokine was precipitated three times with cold acetone, dissolved in RPMI 1640 medium and sterilely filtered through a 0.22 μm filter (Prep. A). Nonmodified native Interferon-α (Prep. B) was used as a control.

B. Antiviral activity of Prep. A and Prep. B was evaluated by suppression of the cytopathic action of vesicular stomatitis virus on kidney cells of pork embryo. Prep. A and Prep. B were added to the cells 24 hours before their infection with a 100-fold lethal dose of the virus. Antiviral effect was determined 24 hours after virus administration. Antiviral titer for Prep. A and Prep. B was determined to be $5 \times 10^7$ and $1 \times 10^4$ respectively.

EXAMPLE 28

Natural human Interferon-$\alpha_2$ was modified with stearoyl chloride and incorporated in block copolymer of poly(oxyethylene)-poly(oxypropylene) in which N=1.30 (Prep. A) as described in Example 25 (Prep. A). Nonmodified B was used as a control.

B. Antiviral activity of Prep. A and Prep. B was evaluated by suppression of the cytopathic action of Aujeszky's disease virus on kidney cells of pork embryo. Prep. A and Prep. B were added to the cells 24 hours before their infection with a 100-fold lethal dose of the virus. Antiviral effect was determined 24 virus administration. Antiviral titer for Pre-A and determined to be $1 \times 10^{10}$ and $2 \times 10^5$ respectively.

EXAMPLE 29

A. Human recombinant Tumor Necrosis Factor-α (TNFα) was incorporated in a block copolymer of poly(oxyethylene)-poly(oxypropylene) in which N=1.00 (pluronic P-85) as descreibed in Example 23 (Prep. A). Nonmodified TNFα (Prep. B) was used as a control.

B. Specific activity of Prep. A and Prep. B with respect to human ovarian carcinoma $SKOV_3$ cells 48 hours. The results were as follows:

| TNFα concentration, nM | Inhibition, % ± SD | |
|---|---|---|
| 0.005 | Prep. A | Prep. B |
| 0.04 | 3.3 ± 0.5 | 2.4 ± 0.5 |
| 0.2 | 24.4 ± 2.7 | 4.8 ± 1.0 |
| 1 | 52.3 ± 4.8 | 4.8 ± 1.0 |
| 5 | 76.7 ± 5.9 | 8.5 ± 1.2 |
| 20 | 84.3 ± 7.9 | 28.6 ± 2.3 |
| 100 | 91.5 ± 8.2 | 40.0 ± 3.6 |
| 150 | 100 ± 11.3 | 65.0 ± 5.7 |

EXAMPLE 30

A. Human recombinant Interleukin-2 (IL-2) was covalently conjugated with a poly(oxyethylene)-poly(oxypropylene) block copolymer wherein N=1.00 (pluronic P-85) containing terminal aldehyde groups. To this end, 10 μg of IL-2 were incubated over 4 hours at room temperature with the 50-fold molar excess of the block-copolymer in the presence of 50-fold molar excess of cyanoborhydride in 0.1 M borate buffer (pH 8.5). The conjugate was purified by gel-filtration on Biogel P-4 and then incorporated in the micelles of block-copolymer of poly(oxyethylene)-poly-(oxypropylene) in which N=1.00 (pluronic P-85). Example 23 (Prep. A). Nonmodified IL-2 was used as a control (Prep. B).

B. The specified activity of IL-2 in Prep. A and Prep. B was determined using the IL-2 dependent CTLL2 cell line as described by Gillis, et al., *J. Immunol.*, 120, 2027 (1978). The IL-2 activity was equal to $36 \times 10^6$ units/μg in Prep. A and $5 \times 10^6$ units/μg in Prep. B.

EXAMPLE 31

A. Natural human Interferon-$\alpha_2$ was modified with stearoyl chloride and incorporated in block copolymers of poly(oxyethylene)-poly(oxypropylene) in which N=1.30 (Prep. A) as described in Example 26 (Prep. A). Nonmodified native is used as a control. Interferon-$\alpha_2$ (Prep-B).

B. Groups of C57B1/6–7 week-old male mice which included 36 animals/group were infected (intranasally) with a 10-fold lethal dose of influenza virus H/Chili/1/83 (H1N1. Equal doses of Prep. A and Prep. B were introduced subcutaneously 24 hours after infecting the animals. Survivability of animals was observed during 30 days following drug administration. On the 30th day, the survivability of animals in the control group of nontreated animals was equal to 0%; in the group treated with Prep. A—to 75%; and in the group treated with Prep. B—to 12%.

EXAMPLE 32

A. Natural pork Interferon-$\alpha_2$ was modified with stearoyl chloride and incorporated in poly(oxyethylene)-poly(oxypropylene) block copolymers in which N=1.30 (Prep. A) as described in Example 25 (Prep. A). Nonmodified native Interferon-$\alpha_2$ (Prep. B) was used as a control.

B. Groups of 3-month old white piglets (8 animals/group) not vaccinated against Aujeszky's disease were infected intracerebrally with a 1000-fold $LD_{50}$ of Aujeszky's disease virus (virulent strain "Arsky"). Prep. A and Prep. B were administered three times intramuscularly: 24 hours before, simultaneously with and 24 hours after infection in doses of 0.01 mg, 0.1 mg and 10 mg per animal per injection. Survivability and Aujeszky's disease symptoms were observed during a 60 day period. In the control experiment the same group of untreated infected animals was studied. The results obtained were as follows:

| Sample | Dose (mg per animal) | Survivability in a group, % | Sick rate in a group, % |
| --- | --- | --- | --- |
| Prep. A | 3 × 0.01 | 100 | 0 |
| Prep. A | 3 × 0.1 | 100 | 0 |
| Prep. B | 3 × 0.1 | 0 | 100 |
| Prep. B | 3 × 0.1 | 12.5 | 100 |
| Control (untreated cells) | — | 0 | 100 |

[a]Aujeszky's disease manifestations included disorders of the central nervous system, convulsions, paralysis of gullet, larynx and extremities. The percentage of animals that contracted the disease is presented.

EXAMPLE 33

Prep. A and Prep. B were the same as in Example 31. Groups of 4-month old piglets (11 animals/group) not vaccinated against Aujeszky's disease, were infected intracerebrally with a 10000-fold $LD_{50}$ of Aujeszky's disease virus (virulent strain "Arsky"). Prep. A and Prep. B were administered at the serious stage of the disease three times intramuscularly: on days 6, 8, 10 after infection in the following doses: 0.01 mg, 0.1 mg and 1.0 mg per animal per injection. Survivability and Aujesztky's disease symptoms were observed during a 60 day period. The results were as follows:

| Sample | Dose (mg per animal) | Survival rate % |
| --- | --- | --- |
| Prep. B | 3 × 1.0 | 0 |
| Prep. A | 3 × 0.01 | 73 |
| Control (untreated animals) | — | 0 |

EXAMPLE 34

Solution Behavior of Poly(oxyethylene)-Poly(oxypropylene) Block Copolymers

Poly(oxyethylene)-poly(oxypropylene) block copolymers were dissolved in the phosphate-bufferred saline, 10 μM, pH 7.4 (PBS) or in 2.5% solution of bovine serum albumin (BSA) in PBS at the concentrations shown below, and the mixtures incubated for at least one hour at 22.5° C. or 37° C. After that the effective diameters of the aggregates formed in these systems were measured by quasielastic light scattering method as described by Kabanov et al., Macromolecules 28, 2303–2314 (1995). The results were as follows:

| Copolymer | Conc., % | T, ° C. | Effective diameter, nm − BSA | Effective diameter, nm + BSA | Comments |
| --- | --- | --- | --- | --- | --- |
| Pluronic L61 | 0.05 | 22.5 | ND | 10.6 | |
| | 0.1 | 22.5 | ND | 23.4 | |
| | 0.25 | 22.5 | ND | 48.8 | |
| | 0.5 | 22.5 | ND | 138.3 | |
| | 0.005 | 37 | ND | 138 | |
| Pluronic L61 | 0.006 | 37 | ND | — | |
| | 0.008 | 37 | 336 | — | |
| | 0.01 | 37 | 455 | 120 | |
| | 0.025 | 37 | 960 | (*) | |
| | 0.04 | 37 | | (*) | |
| | 0.05 | 37 | 1265 | (*) | |
| | 0.075 | 37 | 1120 | (*) | |
| | 0.1 | 37 | LPS | LPS | |
| | 0.25 | 37 | LPS | LPS | |
| | 0.5 | 37 | LPS | LPS | |
| Pluronic L81 | 0.04 | 22.5 | — | 13.8 | |
| | 0.1 | 22.5 | ND | 20.6 | |
| | 0.25 | 22.5 | ND | 379 | Very cloudy solution with BSA |
| | 0.5 | 22.5 | 935 | — | Very cloudy solutions |
| | 0.01 | 37 | — | 266 | |
| | 0.04 | 37 | 1004 | (*) | |
| | 0.06 | 37 | (*) | (*) | |
| | 0.08 | 37 | (*) | (*) | |
| Pluronic L121 | 22.5 | 0.01 | — | 541.5 | |
| | 22.5 | 0.05 | — | 330 | |
| Pluronic F44 | 22.5 | 0.5 | ND | 12.9 | |
| | 22.5 | 1.0 | ND | 11.7 | |
| | 22.5 | 2.25 | ND | 14.2 | |
| | 22.5 | 4.5 | ND | 28.7 | |
| | 22.5 | 7.5 | ND | — | |
| | 22.5 | 10.0 | ND | 105 | |
| | 37 | 0.5 | ND | 84.4 | |
| | 37 | 1.0 | ND | 97.1 | |
| | 37 | 2.25 | ND | 137 | |
| | 37 | 5.0 | ND | 68.1 | |
| | 37 | 7.5 | ND | | |
| | 37 | 10.0 | 12.3 | 69.4 | |
| Pluronic L64 | 0.5 | 22.5 | ND | 10.8 | |
| | 1.0 | 22.5 | ND | 12 | |
| | 5.0 | 22.5 | ND | 21.6 | Opalescence and smell fraction of |

-continued

| Copolymer | Conc., % | T, °C. | Effective diameter, nm − BSA | Effective diameter, nm + BSA | Comments |
|---|---|---|---|---|---|
| | 0.1 | 37 | ND | 36.2 | aggregates (85 nm) with BSA |
| | 0.5 | 37 | 240 | 192.5 | Slightly cloudy solution without BSA and very cloudy solution with BSA |
| | 1.0 | 37 | 16.6 | 11.6 | |
| | 5.0 | 37 | 13.1 | 11.3 | |
| Pluronic P85 | 22.5 | 0.5 | ND | — | |
| | 22.5 | 1.0 | ND | 12.9 | |
| | 22.5 | 5.0 | ND | 18.7 | |
| | 37 | 0.5 | 13.9 | — | |
| | 37 | 1.0 | 12.6 | 79.6 | |
| | 37 | 5.0 | 12.8 | 109 | |
| Pluronic F108 | 37 | 2.0 | — | 22.8 | — |
| Pluronic F127 | 37 | 1.0 | — | 23.2 | — |
| | 37 | 2.0 | — | 21.5 | — |
| Tetronic T1307 | 22.5 | 2.0 | — | ND | — |
| | 37 | 0.5 | — | 16.7 | — |
| | 37 | 1.0 | — | 17.1 | — |
| | 37 | 2.0 | — | 16.6 | 37.4 |

"ND": Non Detectable
"LPS": Liquid Phase Separation.
(*) Turbidity was too high for light scattering measurements.

The results suggest that (1) hydrophobic poly(ethylene oxide)-poly(propylene oxide) block copolymrs with propylene oxide content not less than 50% (w/v) reveal tendency for aggregation in aqueous solutins at physiological temperature, (2) aggregation and phase separation of these copolymers is significantly enhanced in the presence of serum proteins.

EXAMPLE 35

Effects of Hydrophilic Pluronic Copolymers on Solution Behavior of Hydrophobic Pluronic Copolymers.

the same procedure as in Example 34, but substituting a mixture of two different poly(propylene oxide) block copolymers for the single copolymer. The results were as follows:

| First Copolymer (conc. %) | Second conc., % | T, °C. | Effective diameter, nm − BSA | Effective diameter, nm + BSA |
|---|---|---|---|---|
| Pluronic L121 | Pluronic F127 (0.5) | 22.5 | 116.4 | |
| | Pluronic F127 (1.0) | 22.5 | 113.9 | |
| | Pluronic F127 (5.0) | 22.5 | 313.2 | |
| | Pluronic F127 (0.5) | 37 | 88.7 | |
| Pluronic L121 (0.1) | Pluronic F127 (1.0) | 37 | 77.1 | |
| | Pluronic F127 (2.0) | 37 | 177 | |
| | Pluronic F127 (5.0) | 37 | 262 | |
| Pluronic L61 (0.1) | Pluronic F127 (0.5) | 37 | 26.7 | 23.8 |
| | Pluronic F127 (1.0) | 37 | 23.6 | 12.9 |
| | Pluronic F127 (2.0) | 37 | 21.6 | 13.8 |
| Pluronic L61 (0.125) | Pluronic F127 (1.0) | 37 | 24.7 | 53 |
| | Pluronic F127 (2.0) | 37 | 22.3 | — |
| Pluronic L61 (0.25) | Pluronic F127 (0.5) | 37 | (*) | — |
| | Pluronic F127 (1.0) | 37 | (*) | — |
| | Pluronic F127 (2.0) | 37 | 22.4 | 15.0 |
| Pluronic L61 (0.25) | Pluronic F108 (2.0) | 37 | 840 | — |
| Pluronic L61 (0.1) | Tetronic T1307 (1.0) | 37 | (*) | — |
| | Tetronic T1307 (1.5) | 37 | 915.4 | — |
| | Tetronic T1307 (2.0) | 37 | 16.3 | 624.8 |
| Pluronic L61 (0.15) | Tetronic T1307 (2.0) | 37 | 387.4 | — |
| Pluronic L61 (0.2) | | 37 | 520 | — |
| Pluronic L61 (0.25) | | 37 | 735.3 | — |
| Pluronic L61 (0.1) | Tetronic T1307 (2.5) | 37 | — | 522.3 |
| | Tetronic T1307 (3.0) | 37 | | 225 |
| | Tetronic T1107 (2.0) | 37 | (*) | |

"ND": Non-Detectable.
(*) Turbidity was too high for light scattering measurements.

These results suggest that, (1) hydrophilic poly (oxyethylene)-poly(oxypropylene) block copolymers with ethylene oxide content more than 50% (w/v) prevent aggregation of hydrophobic hydrophilic Poly(oxyethylene)-poly (oxypropylene) block copolymers with propylene oxide content not less than 50% (w/v) at physiological temperatures; (2) hydrophilic poly(oxyethylone)-poly (oxypropylene) block copolymers with ethylene oxide content more than 50% (w/v) prevent aggregation of hydrophobic hydrophilic poly(oxyethylene)-poly (oxypropylene) block copolymers with propylene oxide content not less than 50% in the presence of serum proteins.

EXAMPLE 36

Kinetics of Daunorubicin Accumulation

Figure 2:
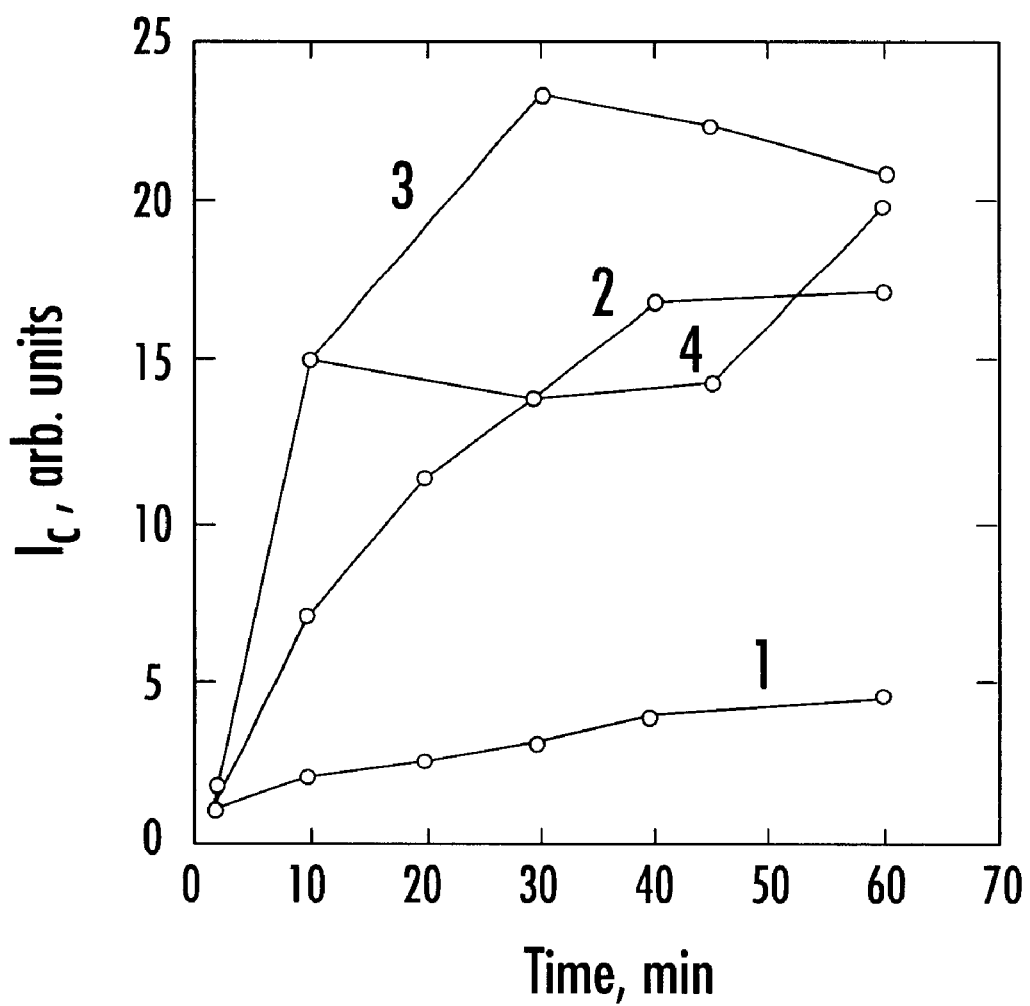
FIG. 2 shows the kinetics of daunorubicin accumulation for SK-resistant cells or SK cells, respectively, treated with daunorubicin in free or micellular form.

The kinetics of daumorubicin accumulation in SK cells and SK-resistant cells was measured for cells treated with daunorubicin at 10 ng/ml by measuring the daunorubicin florescence accumulated in the cells ($\lambda_{ex}$=471 nm, $\lambda_{em}$=556 nm). The drug accumulation data for SK-resistant cells is displayed in in FIG. 2 (line 1: free drug; line 2: micellar form); the data for SK cells is also displayed in FIG. 2 (line 3: free drug; line 4: micellar form).

EXAMPLE 37

Polymer Biodistribution

Radioactive, tritum-containing derivatives of Pluronic P85 polymers were obtained from Kurchatov Institute of Atomic Energy, Moscow, Russia. 100 μl per 20 g of body weight of a 1% w/v isotonic solution of the radioactive copolymer ($2 \times 10^7$ cpm/20 g body weight) was administered i.v. into (a) BALB/c mice (from Kriukovo Veterinary Dept. of Russian Acad. Medical Sciences, Moscow, Russia) and (b) BALB/c mice into which $3 \times 10^6$ SP2/0$^{dnr}$ murine myeloma cells had been injected subcutaneously 6 weeks previously. The biodistribution of polymer at various times post-injection of the radioactive copolymer was measured by sacrificing treated mice at the various timepoints, excising the tissues listed in the tables below, and quantifying the distribution of radioactivity by liquid scintillation counting. To prepare tissue samples for liquid scintillation counting, samples were placed in 1 ml of tissue solubilizer (available from Serva Chemicals, Germany) and homogenized in the cold. The homogenates were incubated for 14 hours at room temperature, decolorized with 50 μl of 30% hydrogen peroxide, and incubated overnight at room temperature.

For BALB/c mice lacking injected tumor cells, the results were:

|  | Polymer content (% of initial dose per organ) | | |
|---|---|---|---|
| Organ | 73 hours | 92.5 hours | 121 hours |
| Spleen | 0.23 | 0.2 | 0.12 |
| Liver | 3.69 | 3.27 | 1.8 |

For BALB/c mice with injected tumor cells, the results were:

|  | Polymer content (% of initial dose per organ) | | |
|---|---|---|---|
| Organ | 73 hours | 92.5 hours | 121 hours |
| Spleen | 0.35 | 0.47 | 0.36 |
| Liver | 3.71 | 3.35 | 3.35 |
| Tumor | 1.53 | 6.24 | 1.50 |

Additional observations derived from this set of experiments were (1) that degradation products of the polymers were not observed until 24 hours after polymer administration and (2) complete clearance of polymer from the mice occurred 250 to 300 hours after administration.

EXAMPLE 38

Blood concentrations of copolymer

Figure 3:
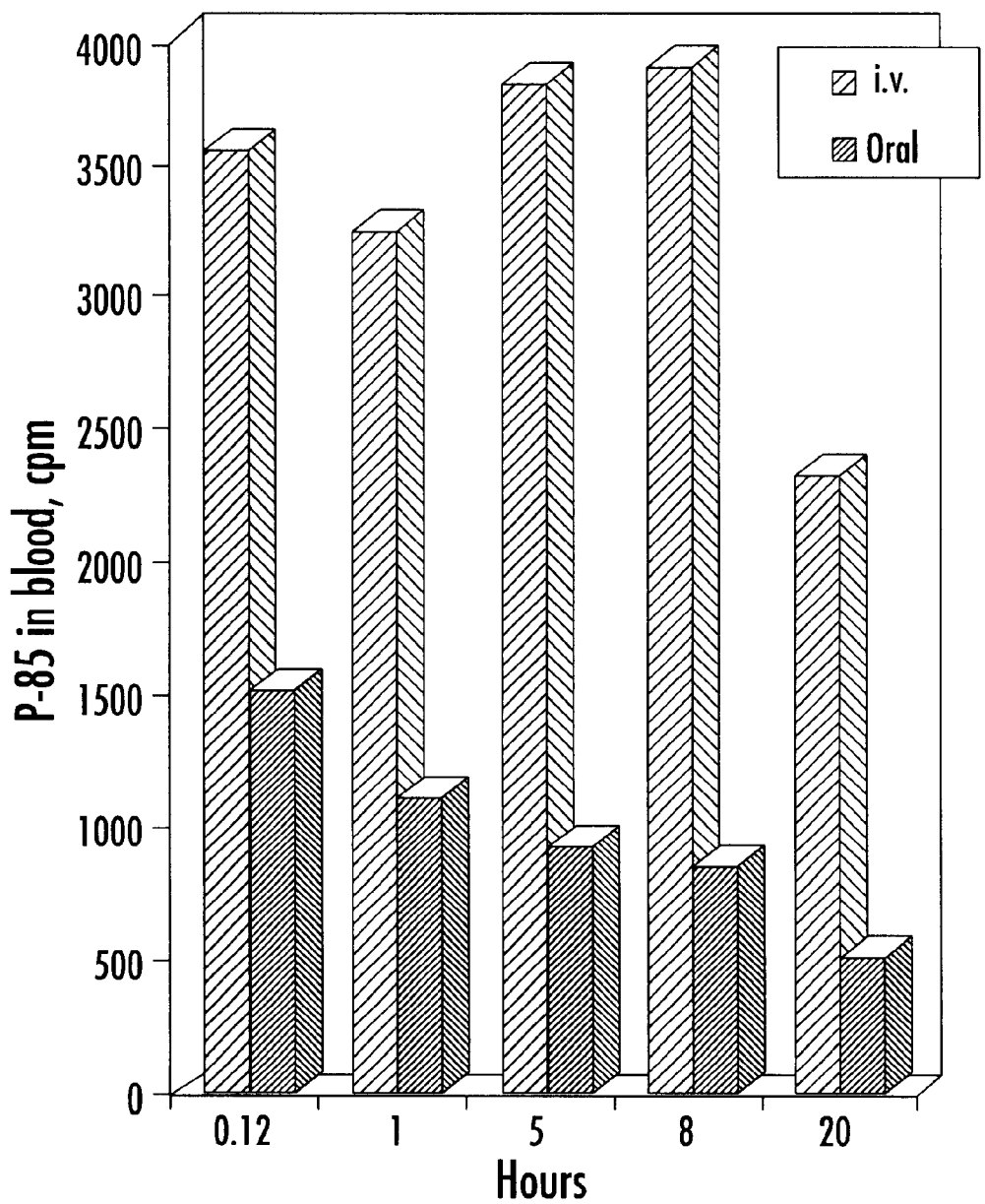
FIG. 3 shows a comparison of the blood concentration of [3H]-Pluronic P85 administered i. v., or orally.

100 μl/20 g body weight of the [$^3$H]—Pluronic P85 of Example 37 were administered to 6-week old BALB/c mice by i.v. injection or orally. The amount of radioactivity found in the blood of the mice at various timepoints post injection is shown in FIG. 3, where the first bar in each pair is for i.v. injected polymer, and the second bar is for orally administered polymer.

EXAMPLE 39

A 1:1.5 mixture of Pluronic P85 and Pluronic L64 having individual ratios (n) of (oxypropylene) to (oxyethylene) blocks of 1.00 and 1.50, respectively, and a combined value (N) of 1.30, was diluted with RPMI 1640 medium to a final concentration of 2.0% at 4° C. The mixture was incubated for 30 minutes at 37° C. and then sterilized by filtration through a 0.22 μm filter. An equal volume of a solution of 200 μg daunorubicin in RPMI 1640 medium was added and this mixture was incubated for 30 minutes at 37° C.

Cytotoxicity to human ovarian cancer cells (CRL 157 cells) was measured, both for this preparation and a parallel preparation of free daunorubicin. The results were as follows:

|  | conc. (ng/mL) | | | | | | |
|---|---|---|---|---|---|---|---|
|  | 50000 | 10000 | 2000 | 400 | 80 | 16 | 3.2 |
|  | % Inhibition | | | | | | |
| Chemotherapeutic drug + Pluronic | 100 | 100 | 100 | 100 | 94 | 53 | 8 |
| Free drug | 100 | 100 | 81 | 50 | 29 | 10 | 2 |

The daunorubicin compositions were evaluated for cytotoxicity in (i) human T-lymphoma (Jurkat) cells and (ii) normal human mononuclear cells. The results were as follows:

|  | conc. (ng/mL) | | | | | | |
|---|---|---|---|---|---|---|---|
|  | 50000 | 10000 | 2000 | 400 | 80 | 16 | 3.2 |
| Cell | % Inhibition | | | | | | |
| Jur.[1] | 100 | 100 | 100 | 100 | 100 | 74 | 28 |
| Jur.[2] | 100 | 100 | 100 | 83 | 59 | 36 | 21 |
| Norm.[1] | 100 | 100 | 91 | 60 | 21 | 5 | 2 |
| Norm.[2] | 100 | 100 | 80 | 58 | 23 | 18 | 1 |

[1]Treated with chemotherapeutic drug + pluronic.
[2]Treated with free (non-micellar) chemotherapeutic drug.

EXAMPLE 40

$IC_{50}$ values for (i) human T-lymphoma (Jurkat) cells and (ii) normal human mononuclear cells were determined for the daunorubicin composition of Example 39 and compared to those for free daunorubicin. Measurements were made at the indicated intervals of the drug contact with the cells. The results were as follows:

|  | time (hours) | | | | | | | |
|---|---|---|---|---|---|---|---|---|
|  | 0.25 | 0.50 | 0.75 | 1.0 | 2.0 | 4.0 | 8.0 | 12 |
| Cell | $IC_{50}$ (ng/mL) | | | | | | | |
| Jur.[1] | 150 | 46 | 25 | 17 | 9.0 | 0.80 | 0.50 | 0.30 |
| Jur.[2] | 120 | 68 | 35 | 25 | 19 | 16 | 3.0 | 5.2 |
| Norm.[1] | 3570 | 950 | 620 | 450 | 250 | 220 | 160 | 140 |
| Norm.[2] | 4900 | 980 | 405 | 310 | 290 | 275 | 280 | 240 |

[1]Treated with chemotherapeutic drug + pluronic.
[2]Treated with free (non-micellar) chemotherapeutic drug.

EXAMPLE 41

The antineoplastic agent vinblastine was incorporated into the block copolymer mixture described in Example 39. The $IC_{50}$ of this preparation against SK cells was determined to be 0.121 μg/mL; the $IC_{50}$ against SK-resistant cells was 0.0012 μg/rmL. The $IC_{50}$ values for free vinblastine were determined to be 0.095 μg/mL against SK cells and 0.615 μg/mL against SK-resistant cells.

EXAMPLE 42

The antineoplastic agent mitomycin C was incorporated into the block copolymer mixture described in Example 39.

The $IC_{50}$ of this preparation against SK cells determined to be 0.265 μg/ml; the $IC_{50}$ against SK-resistant cells was 0.005 μg/mnL. The $IC_{50}$ of free mitomycin C against SK cells was determined to be 0.320 μg/mL; the $IC_{50}$ against SK-resistant cells was 1.120 μg/mL.

EXAMPLE 43

The antineoplastic agent methotrexate was incorporated into the block copolymer mixture described in Example 39. The $IC_{50}$ of this preparation against SK cells was determined to be 0.880 μg/mL; the $IC_{50}$ against SK-resistant cells was 0.0175 μg/mL. The $IC_{50}$ of free methotrexate against SK cells was determined to be 1.090 μg/mL and against SK-resistant cells was 1.340 μg/mL.

EXAMPLE 44

The antineoplastic agent colchicine was incorporated into the block copolymer mixture described in Example 39. The $IC_{50}$ of this preparation against SK cells was determined to be 0.720 μg/mL; the $IC_{50}$ against SK-resistant "SKVLB" cells was 0.045 μg/mL. The $IC_{50}$ of free colchicine against SK cells was determined to be 0.950 μg/mL; and against SK-resistant cells was 7.450 μg/mL.

EXAMPLE 45

The antineoplastic agent daunorubicin was incorporated into the block copolymer mixture described in Example 39. The $IC_{50}$ of this preparation against SKOV3 cells were determined to be 0.600 μg/mL; the $IC_{50}$ against SKOV3 resistant cells was 0.0068 μg/mL. The $IC_{50}$ of free daunorubicin against SKOV3 cells was determined to be 0.620 μg/mL, and against SKOV3-resistant cells was 5.850 μg/mL.

What is claimed:

1. A composition for the delivery of biologically active agents comprising a mixture of poly(oxyethylene)-poly(oxypropylene) block copolymers and at least one biologically active agent, and wherein the mixture comprises at least one block copolymer with ethylene(oxide) content of 50% or less, and at least one block copolymer with ethylene (oxide) content of 50% or more.

2. The composition according to claim 1, wherein at least one of the blockcopolymers is of the formula:

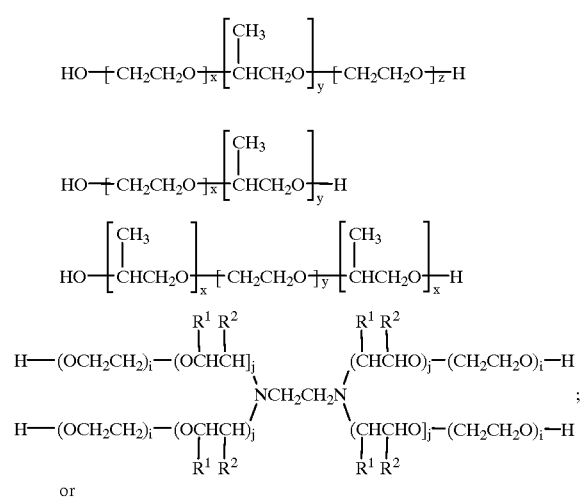

3. A composition for the delivery of a biologically active agent, or derivative thereof, comprising a biologically active agent, or derivative thereof, and a mixture of poly(oxyethylene)-poly(oxypropylene) block copolymers wherein at least one of the block copolymers is of the formula:

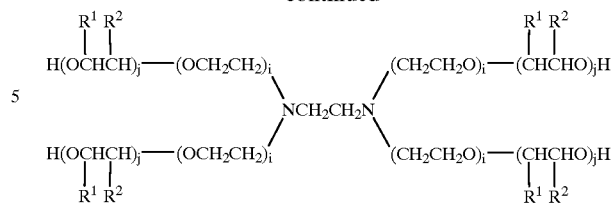

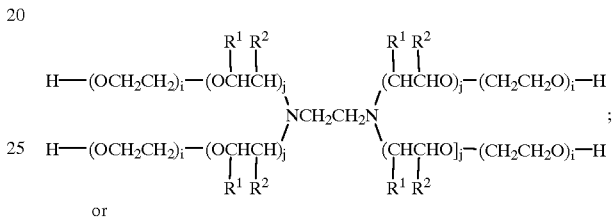

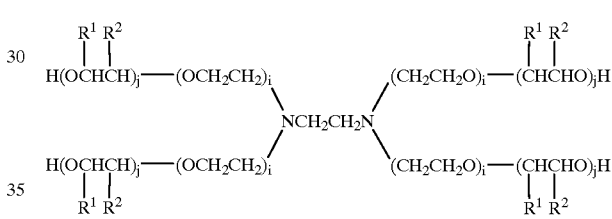

wherein for each $R^1$, $R^2$ pair, one is hydrogen and the other is a methyl group.

4. A composition for the delivery of a biologically active agent, or derivative thereof comprising a biologically active agent, or derivative thereof, and a mixture of poly(oxyethylene)-poly(oxypropylene) block copolymers wherein at least one of the block copolymers is of the formula:

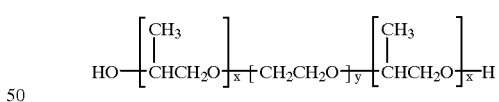

in which x, y, and z have values from about 2 to about 800.

5. The composition according to claim 1, wherein the ratio by weight of the block copolymer with ethylene(oxide) content of 50% or less to the block copolymer with ethylene (oxide) content of 50% or more is 1:2.

6. The composition according to claim 1, wherein the ratio by weight of the block copolymer with ethylene(oxide) content of 50% or less to the block copolymer with ethylene (oxide) content of 50% or more is 1:5.

7. The composition according to claim 1, wherein the biologically active agent is selected from the group consisting of immunomodulators, cytokines, hormones, enzymes, tissue plasminogen activators, clotting factors, colony stimulating factors, and erythropoietins.

8. The composition according to claim 7 wherein the hormone is a human growth hormone.

9. The composition according to claim 8 wherein the hormone is insulin.

10. The composition according to claim 1 wherein the biologically active agent is a neuropeptide, or derivative thereof.

11. The composition according to claim 1 wherein the biologically active agent is selected from the group consisting of recombinant soluble receptors and monoclonal antibodies.

12. The composition of claim 1 wherein the biologically active agent is a protein, peptide, or derivative thereof.

13. The composition of claim 1 wherein the biologically active agent or derivative thereof has reduced cellular transport, reduced penetration into tissues, or reduced penetration across biological barriers.

14. The composition of claim 1 wherein the composition forms micelles.

15. The composition of claim 1, wherein the biologically active agent is a nucleic acid molecule.

16. The composition of claim 1, wherein the biologically active agent is a polynucleotide.

17. A composition for the delivery of biologically active agents comprising a mixture of poly(oxyethylene)-poly(oxypropylene) block copolymers and at least one of the following:
  (a) at least one protein, peptide, or derivative thereof, and
  (b) at least one biologically active agent, or derivative thereof having reduced cellular transport, reduced penetration into tissues, or reduced penetration across biological barriers,
  and wherein the mixture comprises at least one block copolymer with ethylene(oxide) content of 50% or less, and at least one block copolymer with ethylene(oxide) content of 50% or more.

18. The composition of claim 17, wherein the composition forms micelles.

* * * * *